(12) United States Patent
Kim

(10) Patent No.: US 12,312,636 B2
(45) Date of Patent: May 27, 2025

(54) **NANOVESICLES DERIVED FROM GENUS *BACILLUS* BACTERIA AND USE THEREOF**

(71) Applicant: MD HEALTHCARE INC., Seoul (KR)

(72) Inventor: Yoon-Keun Kim, Namyangju-si (KR)

(73) Assignee: MD HEALTHCARE INC., Seoul (KR)

( * ) Notice: Subject to any disclaimer, the term of this patent is extended or adjusted under 35 U.S.C. 154(b) by 460 days.

(21) Appl. No.: 16/325,023

(22) PCT Filed: Aug. 7, 2017

(86) PCT No.: PCT/KR2017/008497
§ 371 (c)(1),
(2) Date: Feb. 12, 2019

(87) PCT Pub. No.: WO2018/030732
PCT Pub. Date: Feb. 15, 2018

(65) Prior Publication Data
US 2019/0177783 A1    Jun. 13, 2019

(30) Foreign Application Priority Data

Aug. 12, 2016 (KR) .......................... 10-2016-0102650
Aug. 4, 2017 (KR) .......................... 10-2017-0098860

(51) Int. Cl.
| | | |
|---|---|---|
| C12Q 1/6851 | (2018.01) | |
| A23L 33/135 | (2016.01) | |
| A61K 8/99 | (2017.01) | |
| A61K 9/00 | (2006.01) | |
| A61K 35/742 | (2015.01) | |
| A61P 3/00 | (2006.01) | |
| A61P 29/00 | (2006.01) | |
| A61P 35/00 | (2006.01) | |
| A61P 37/00 | (2006.01) | |
| A61Q 19/00 | (2006.01) | |
| C12Q 1/6883 | (2018.01) | |
| C12Q 1/6886 | (2018.01) | |
| C12Q 1/689 | (2018.01) | |
| A61K 35/00 | (2006.01) | |

(52) U.S. Cl.
CPC .......... *C12Q 1/6851* (2013.01); *A23L 33/135* (2016.08); *A61K 8/99* (2013.01); *A61K 9/007* (2013.01); *A61K 9/0073* (2013.01); *A61K 35/742* (2013.01); *A61P 3/00* (2018.01); *A61P 29/00* (2018.01); *A61P 35/00* (2018.01); *A61P 37/00* (2018.01); *A61Q 19/00* (2013.01); *C12Q 1/6883* (2013.01); *C12Q 1/6886* (2013.01); *C12Q 1/689* (2013.01); *A61K 2035/115* (2013.01); *C12Q 2600/158* (2013.01); *Y02A 50/30* (2018.01)

(58) Field of Classification Search
None
See application file for complete search history.

(56) References Cited

U.S. PATENT DOCUMENTS

| | | | | |
|---|---|---|---|---|
| 8,969,653 | B2 * | 3/2015 | Gho | .......................... A61P 9/10 |
| | | | | 800/9 |
| 9,149,542 | B2 * | 10/2015 | Gho | .......................... A61P 31/12 |
| 2009/0104167 | A1 | 4/2009 | Hattori et al. | |
| 2013/0115241 | A1 | 5/2013 | Gho et al. | |
| 2016/0089403 | A1 | 3/2016 | Kubo | |

FOREIGN PATENT DOCUMENTS

| | | | | |
|---|---|---|---|---|
| CN | 103079592 | A | 5/2013 | |
| EP | 2 494 865 | A2 | 9/2012 | |
| JP | 2003-221342 | A | 8/2003 | |
| JP | 2007-084504 | A | 4/2007 | |
| JP | 2013-503858 | A | 2/2013 | |
| JP | 2013-534830 | A | 9/2013 | |
| KR | 10-2011-0025068 | A | 3/2011 | |
| KR | 10-2011-0025603 | A | 3/2011 | |
| KR | 20110025603 | A * | 3/2011 | ............... A61P 9/10 |
| KR | 10-2011-0082481 | A | 7/2011 | |
| KR | 10-2016-0110232 | A | 9/2016 | |

(Continued)

OTHER PUBLICATIONS

Mayo Clinic. Asthma. Retrieved from the Mayo Clinic Website on Aug. 17, 2023. (Year: 2022).*
Merck Manual Consumer Verision. Kumar, Sonal. Overview of Chronic Hepatitis. Retrieved from the Merck Website on Aug. 17, 2023. (Year: 2022).*
NIH (National Institute of Arthritis and Musculoskeletal and Skin Diseases). Atopic Dermatitis. Retrieved from the NIH Website on Aug. 17, 2023. (Year: 2023).*
Kim, Ji Hyun et al. Gram-negative and Gram-positive bacterial extracellular vesicles. Seminars in Cell & Developmental Biology 40 (2015). Elsevier. pp. 97-104. (Year: 2015).*

(Continued)

*Primary Examiner* — Nghi V Nguyen
(74) *Attorney, Agent, or Firm* — Vorys, Sater, Seymour and Pease LLP; Mih Suhn Koh

(57) ABSTRACT

Provided are vesicles derived from the genus *Bacillus* bacteria and a use thereof. Further, the vesicles are significantly reduced in samples of patients with cancers, such as liver cancer, bladder cancer, breast cancer, and ovarian cancer; inflammatory diseases, such as asthma and atopic dermatitis; or metabolic diseases, such as diabetes and cirrhosis, compared with normal persons, and the vesicles inhibited the secretion of inflammatory mediators by pathogenic vesicles, such as *E. coli*-derived vesicles, which are causative factors of inflammatory diseases, diabetes, and the like. Therefore, the vesicles derived from the genus *Bacillus* bacteria according to the subject matter can be advantageously used for the purpose of developing a diagnostic method for cancer, inflammatory diseases, and metabolic diseases, and a preventive or therapeutic composition therefor.

7 Claims, 18 Drawing Sheets

Specification includes a Sequence Listing.

(56) References Cited

FOREIGN PATENT DOCUMENTS

WO    2015/178653 A1    11/2015

OTHER PUBLICATIONS

Campos, Joao Henrique et al. Extracellular Vesicles: Role in Inflammatory Responses and Potential Uses in Vaccination in Cancer and Infectious Diseases. Journal of Immunology Research vol. (2015). Hindawi Publishing Corporation. pp. 1-14. (Year: 2015).*
The extended European Search Report for corresponding EP Application No. 17839750.1, mailed Dec. 9, 2019, 7 pages.
The Office Action for corresponding EP Application No. 17839750.1, mailed Feb. 10, 2021, 8 pages.
The Office Action for corresponding JP Application No. 2019-507291, mailed Feb. 12, 2020, 7 pages.
The Office Action for corresponding JP Application No. 2019-507291, mailed Aug. 4, 2020, 6 pages.
Schertzer et al., 'Bacterial outer membrane vesicles in trafficking, communication and the host-pathogen interaction, Journal of Molecular Microbiology and Biotechnology, 2013, vol. 23, pp. 118-130.
Xiong et al., "Transcription Factor STAT3 as a Novel Molecular Target for Cancer Prevention", Cancers 2014, 6, 926-957.
Chinese Office Action issued Oct. 20, 2021, for corresponding CN Application No. 201780049499.7, 5 pages.

* cited by examiner

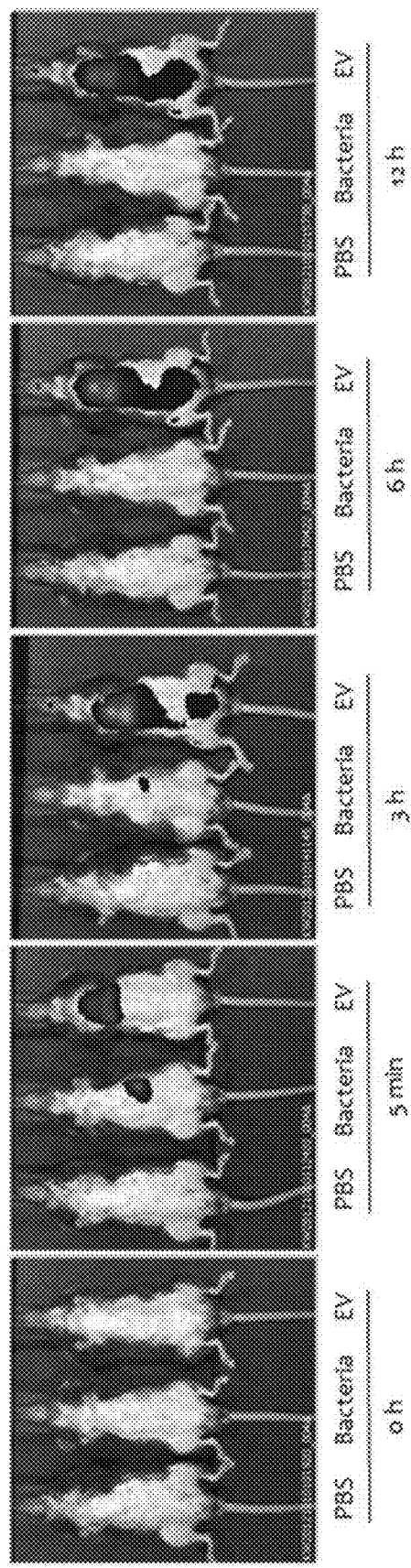
[Fig. 1A]

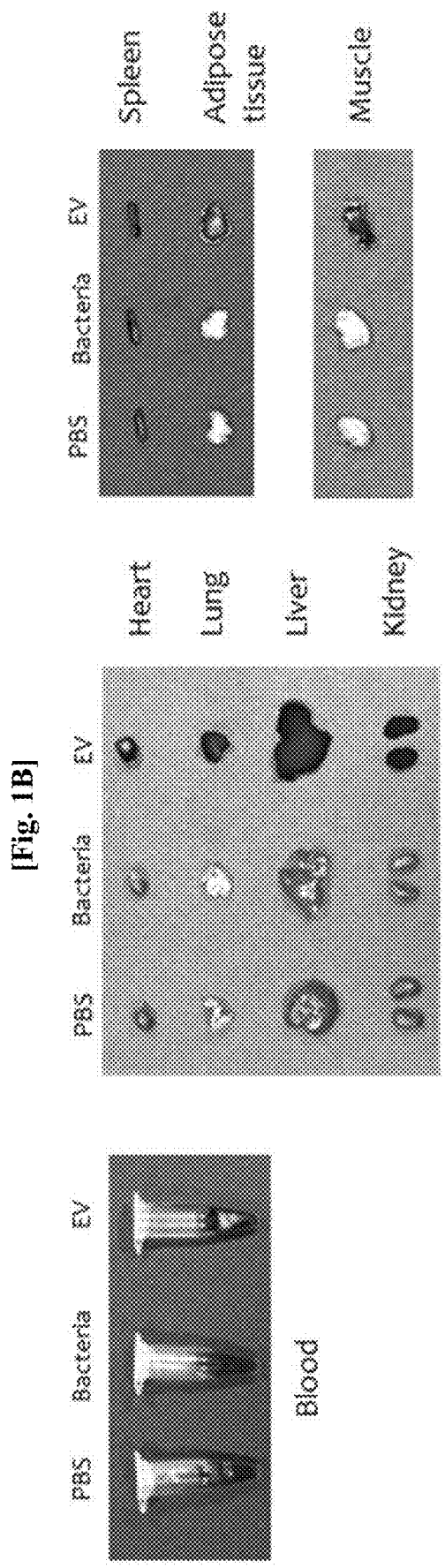
[Fig. 1B]

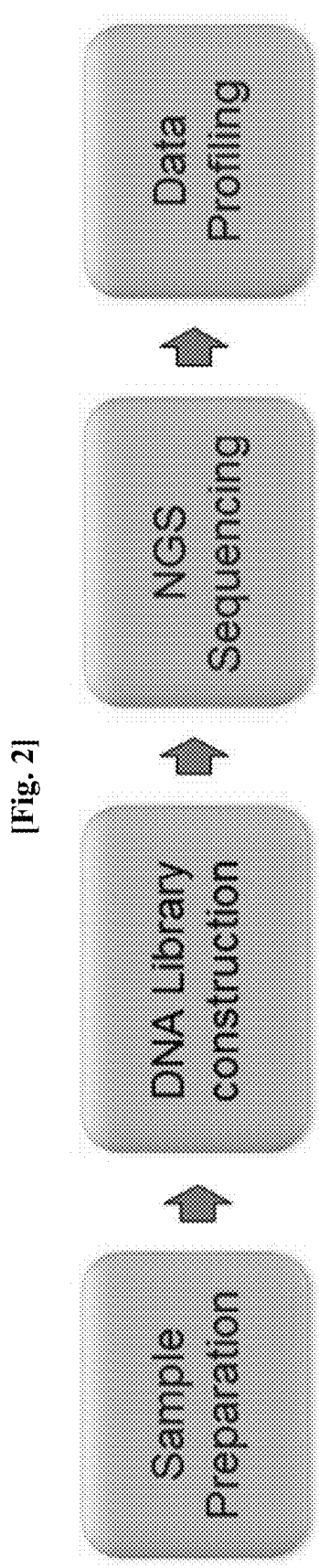
[Fig. 2]

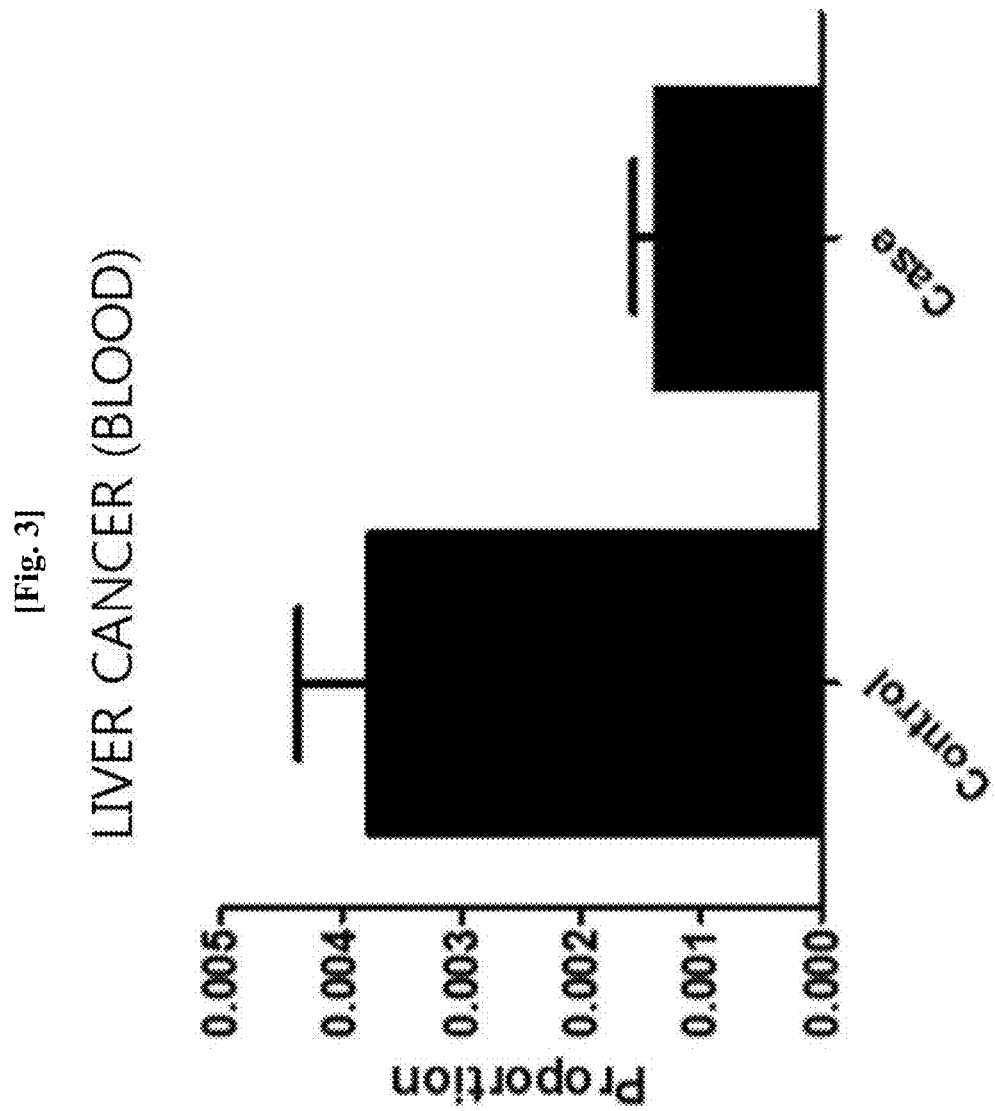
[Fig. 3]

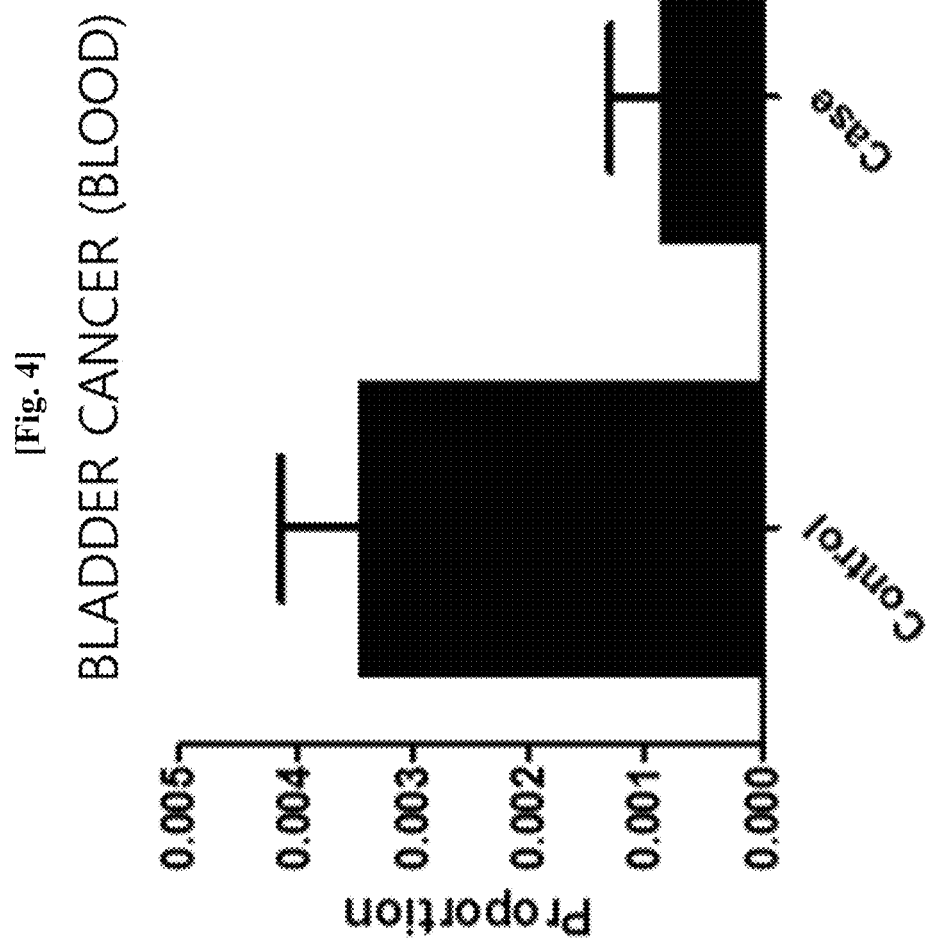
[Fig. 4]

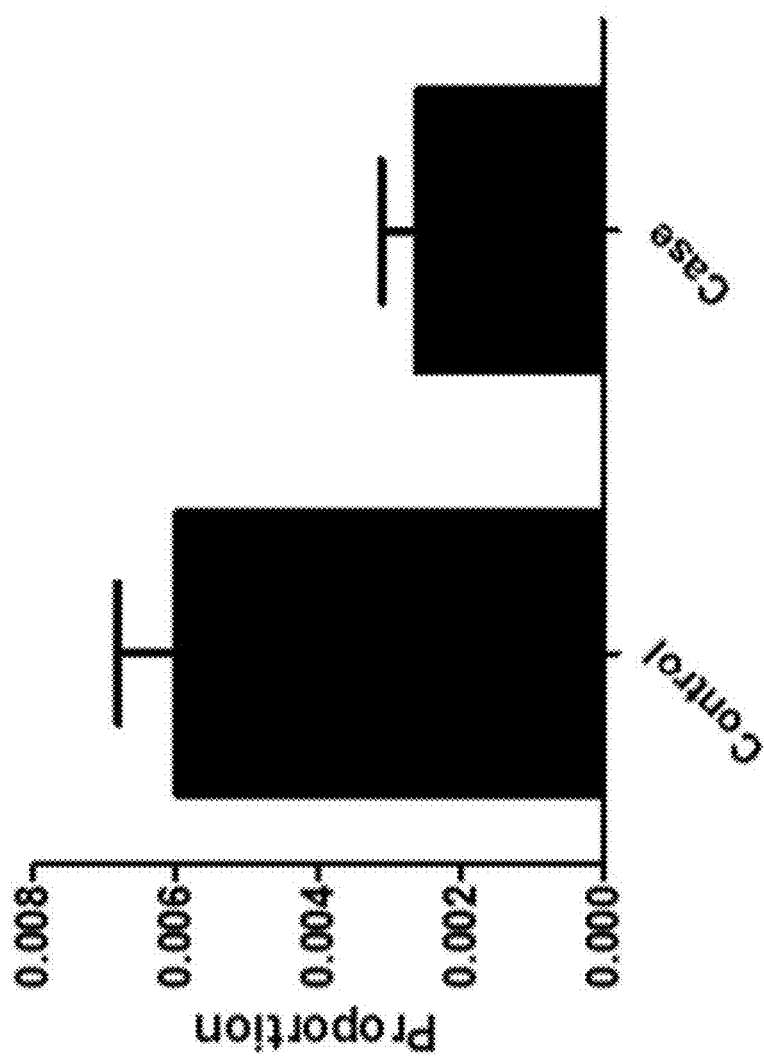
[Fig. 5]

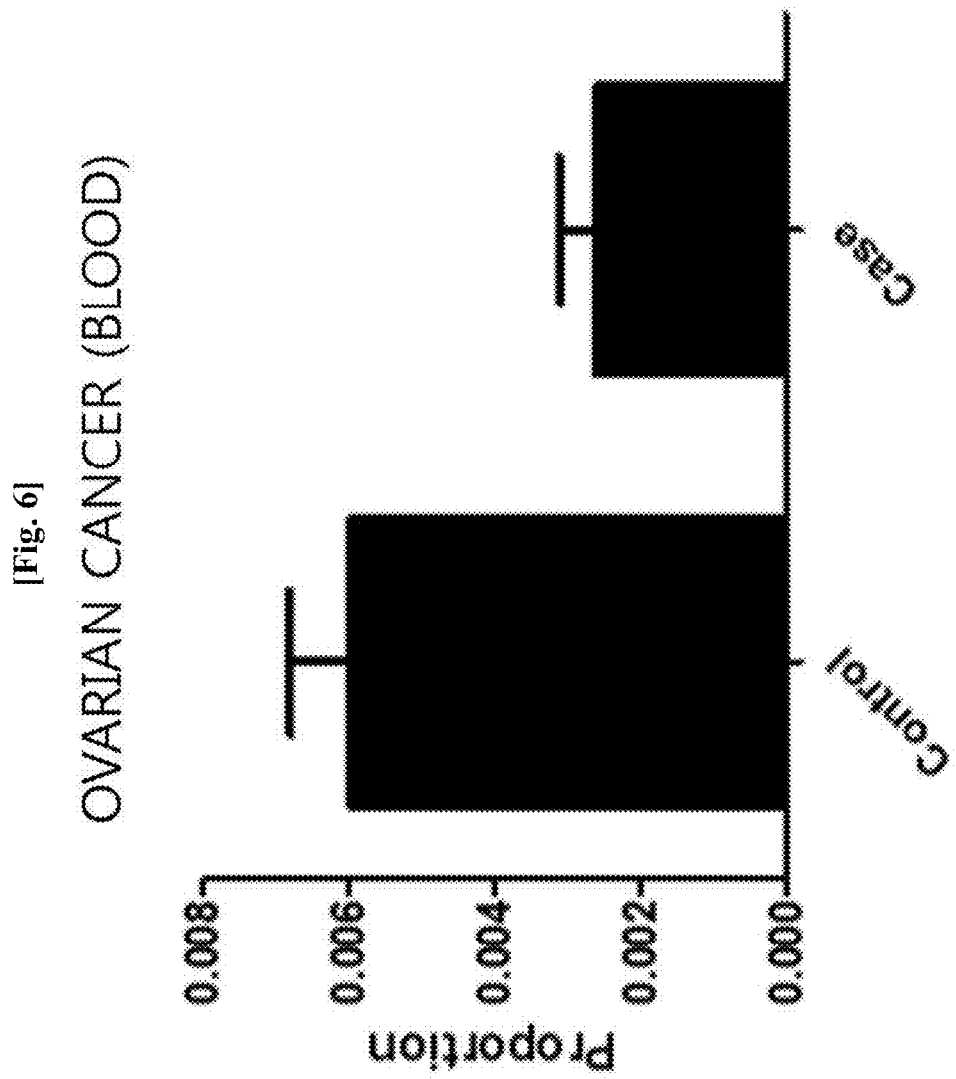
[Fig. 6]

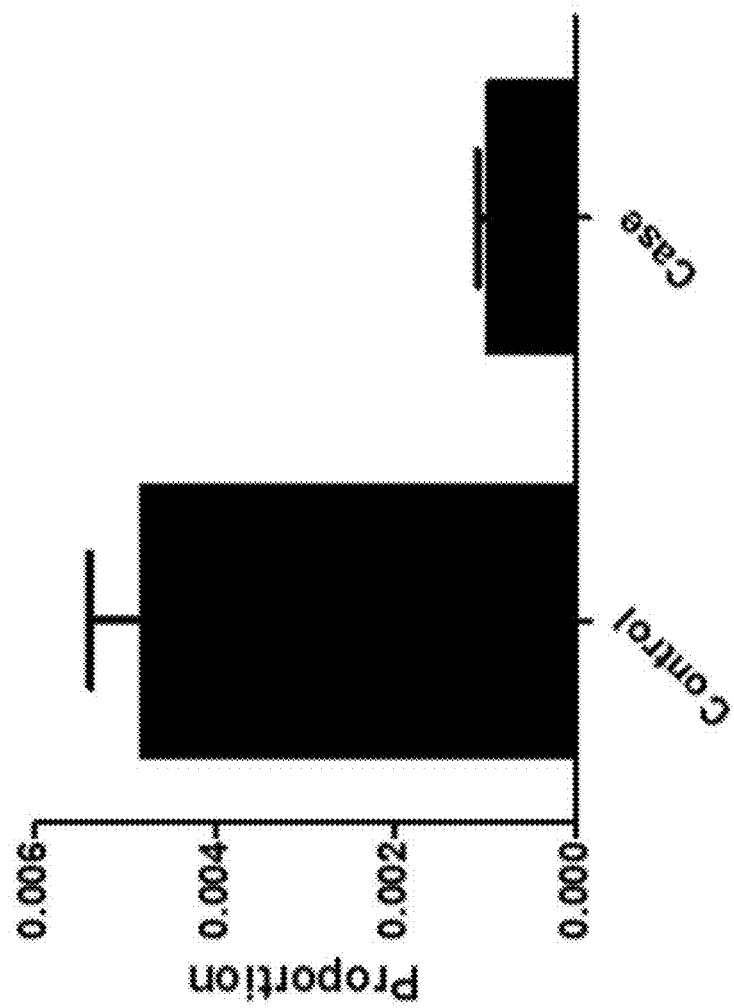
[Fig. 7]

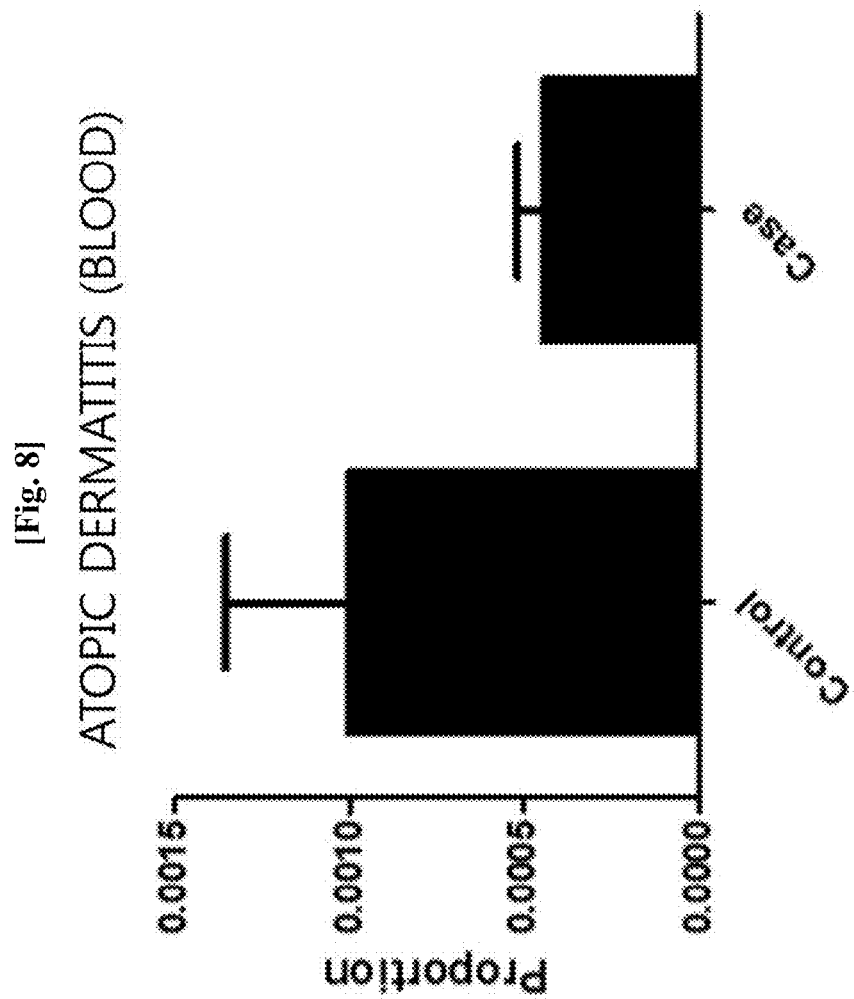

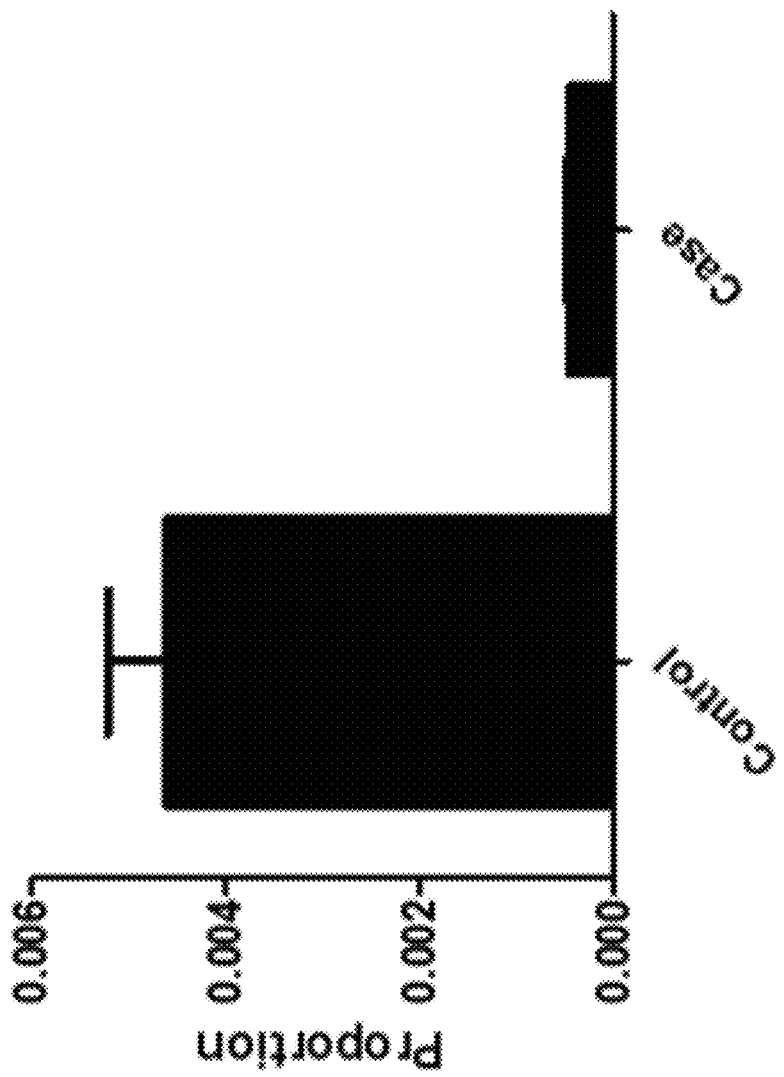
[Fig. 9]

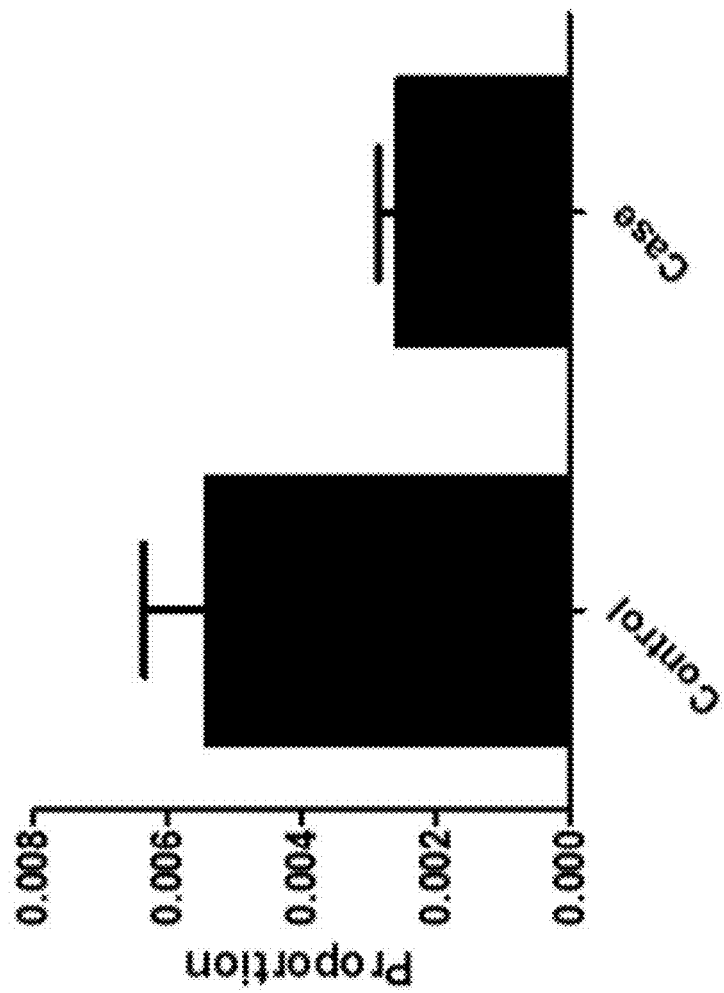
[Fig. 10]

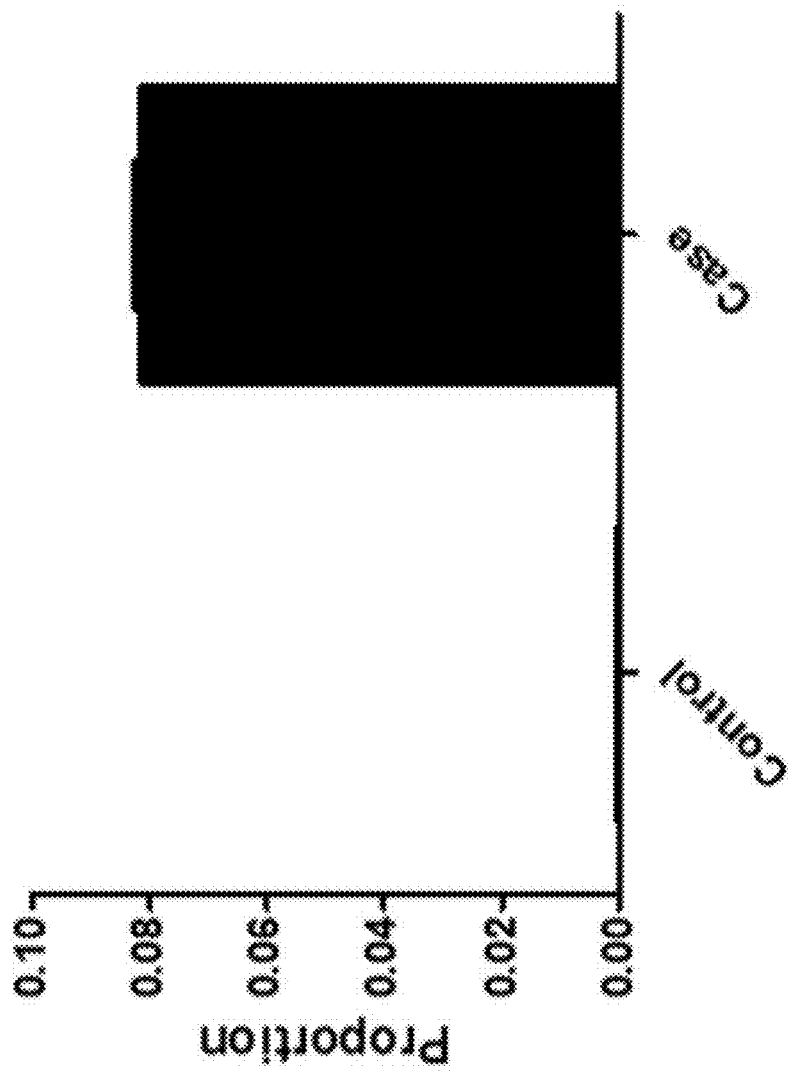

[Fig. 12A] ELECTRON MICROSCOPE (TEM)
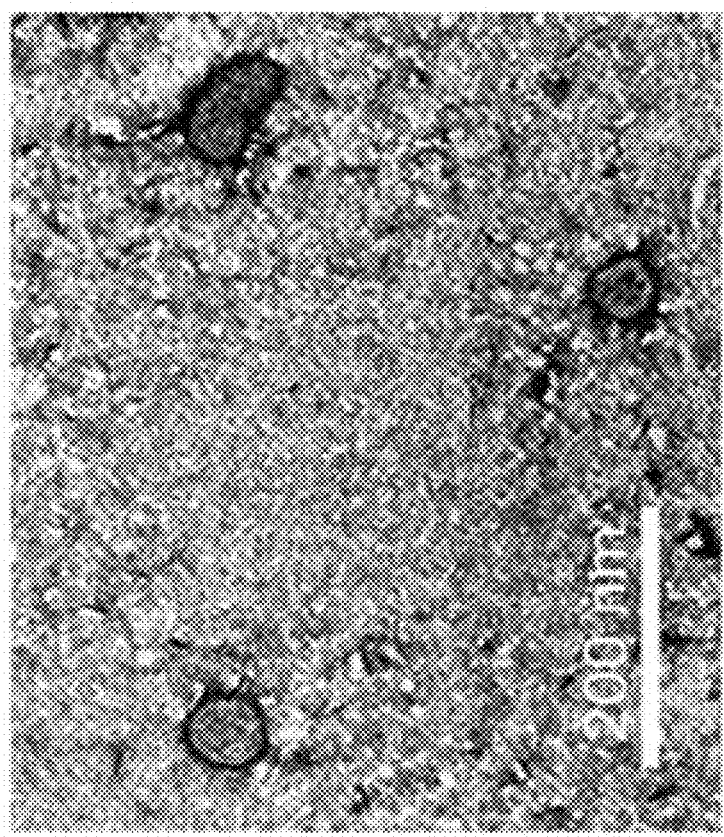

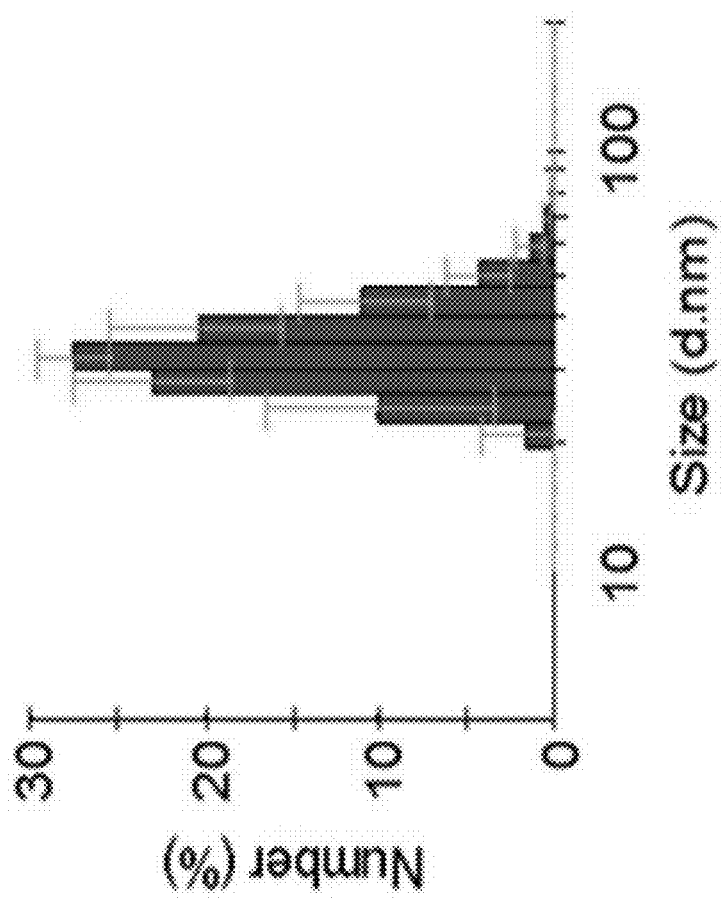
[Fig. 12B]

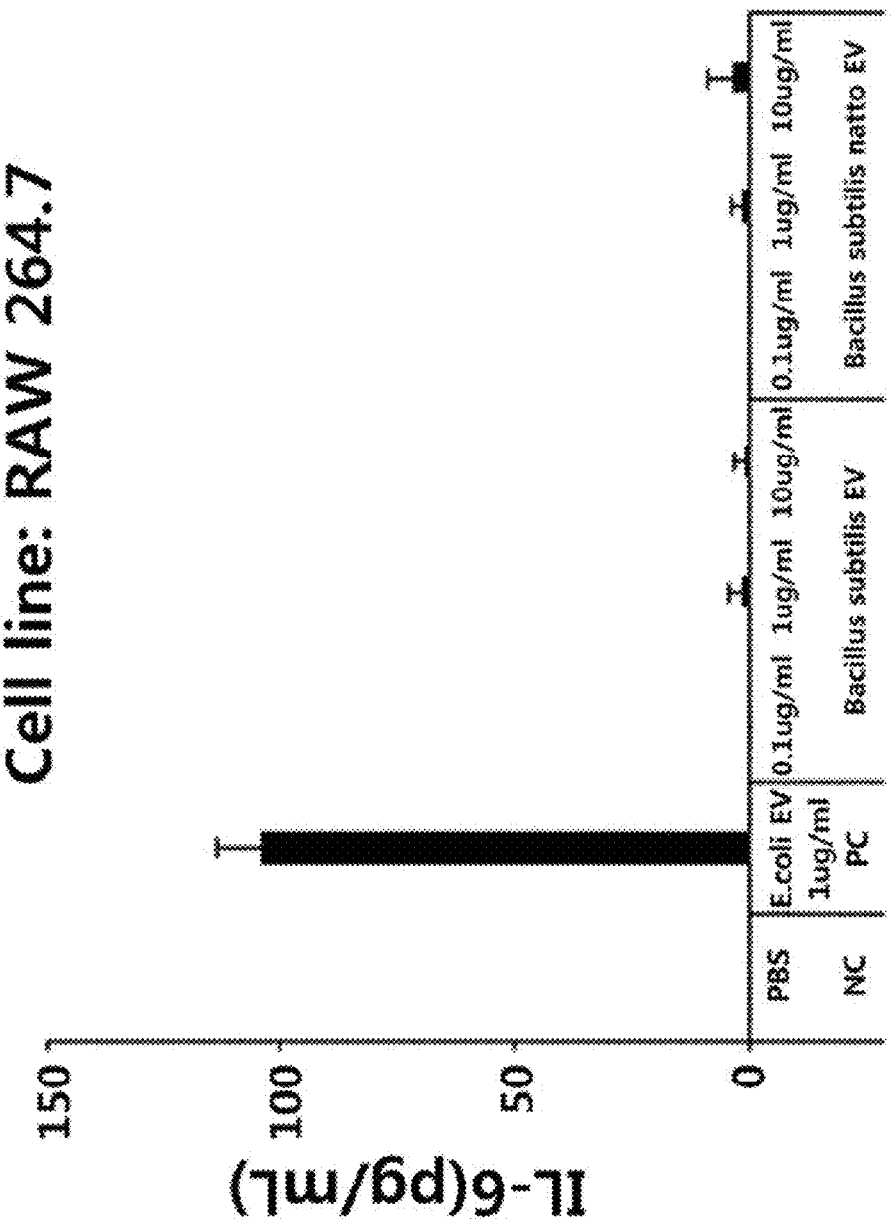
[Fig. 13A]

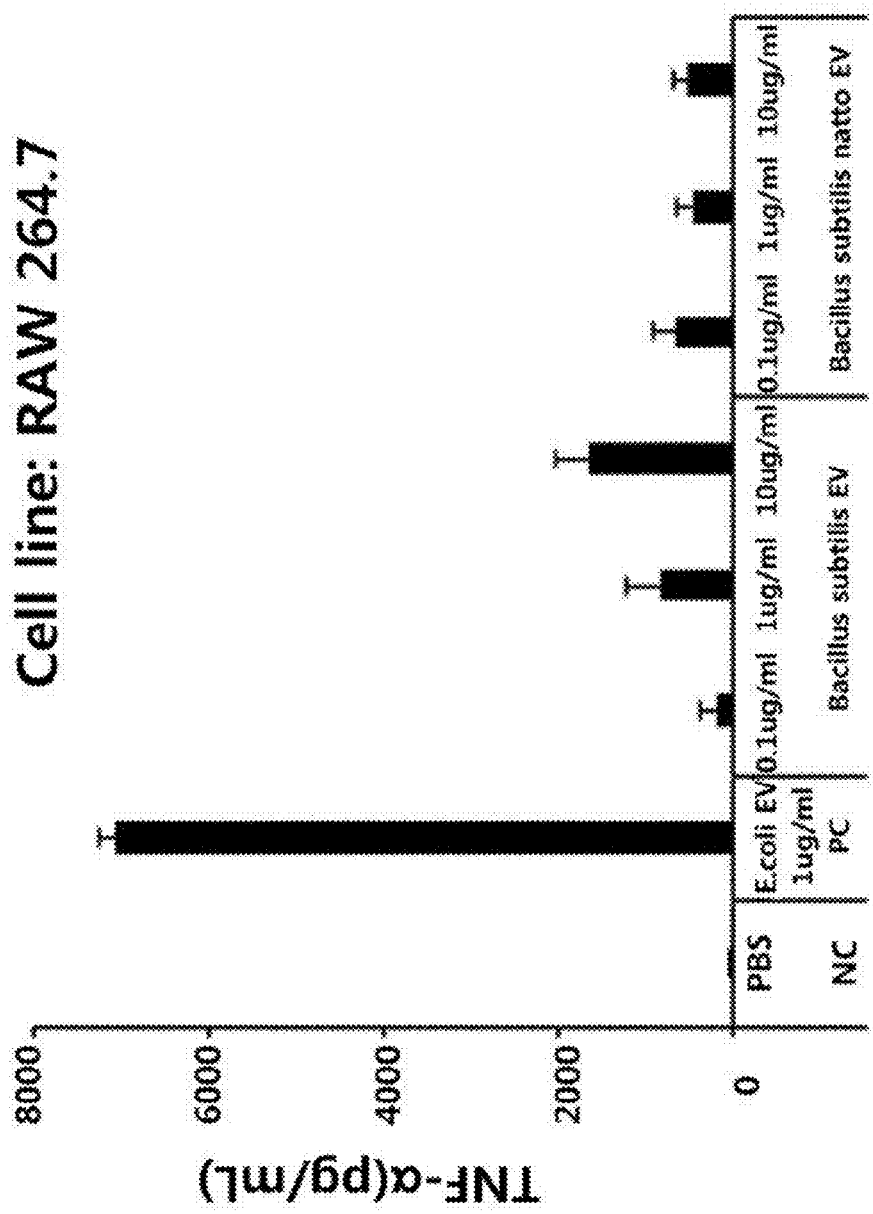
[Fig. 13B]

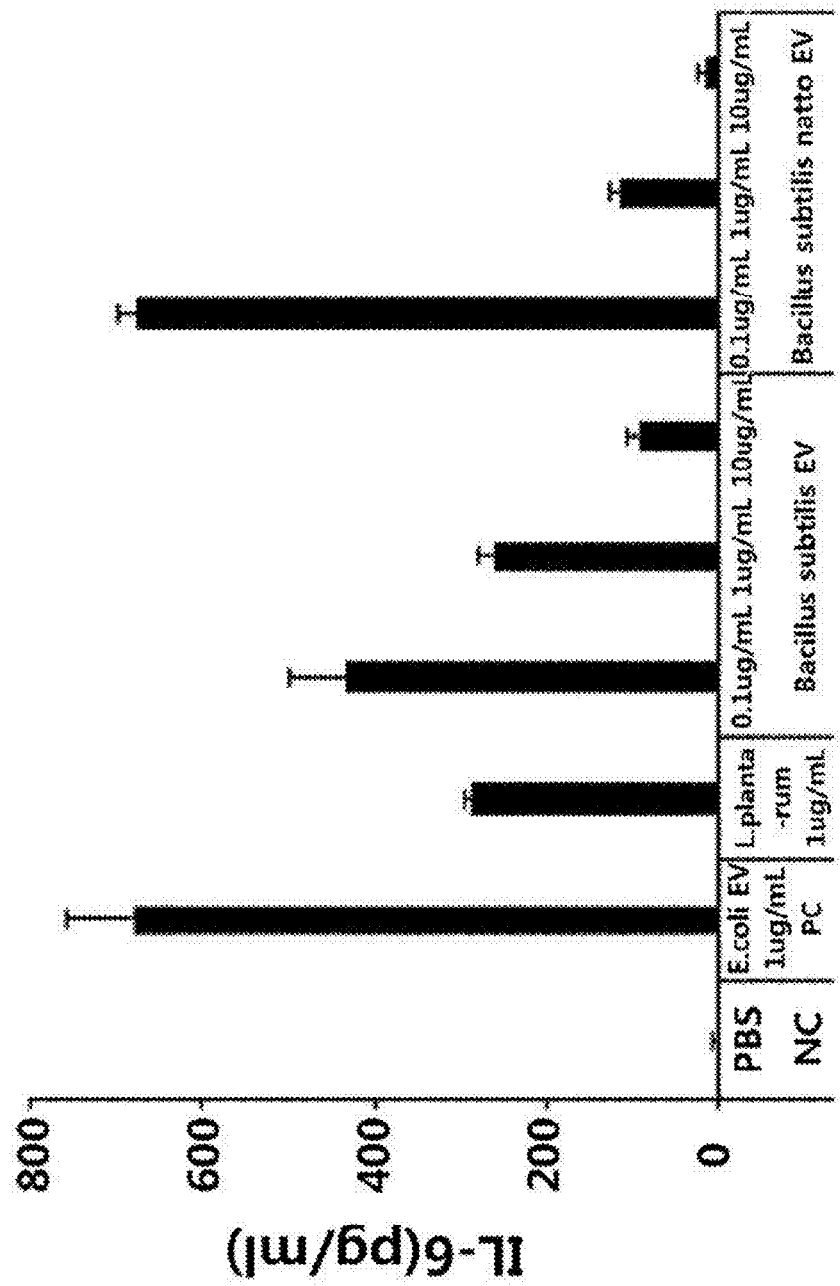
[Fig. 14A]

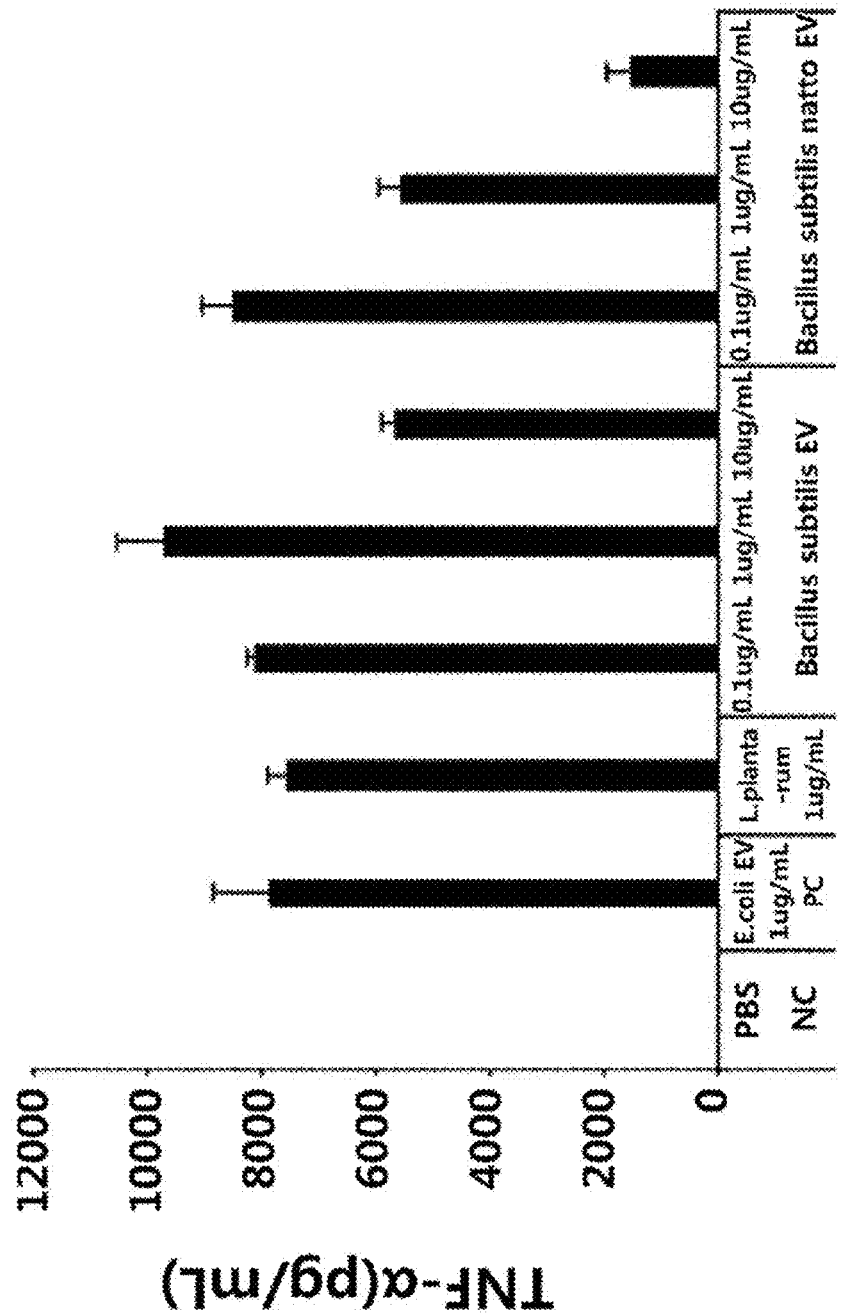
[Fig. 14B]

NANOVESICLES DERIVED FROM GENUS *BACILLUS* BACTERIA AND USE THEREOF

CROSS-REFERENCE TO RELATED APPLICATION

This application is a 371 of PCT/KR2017/008497, filed Aug. 7, 2017, which claims the benefit of priority from Korean Patent Application No. 10-2016-0102650, filed Aug. 12, 2016 and Korean Patent Application No. 10-2017-0098860, filed Aug. 4, 2017, the contents of each of which are incorporated herein by reference in its entirety.

SEQUENCE LISTING

The Sequence Listing submitted in text format (.txt) filed on Feb. 12, 2019, named "SequenceListing.txt", created on Jan. 28, 2019 (766 bytes), is incorporated herein by reference.

TECHNICAL FIELD

The present invention relates to nanovesicles derived from bacteria of the genus *Bacillus* and a use thereof, and more particularly, to a method of diagnosing cancer, an inflammatory disease or a metabolic disease using nanovesicles derived from bacteria of the genus *Bacillus*, and a composition for preventing or treating cancer, an inflammatory disease or a metabolic disease, which includes the nanovesicles.

BACKGROUND ART

Entering the 21$^{st}$ century, while the importance of an acute infectious disease, which was recognized as an epidemic in the past, has become less important, a disease pattern has been changed such that a chronic disease caused by the incompatibility between a human and a microbiome is considered as a main disease which determines the quality of life and a human lifespan. The chronic disease is characterized by chronic inflammation accompanied by immune dysfunction, and cancer, a chronic inflammatory disease, a metabolic disease, etc. are becoming serious problems in the public health.

Inflammation is a local or systemic defense mechanism against damage or infection of cells and tissues, and is generally caused by serial bioreactions occurring due to a direct response of a humoral mediator consisting of an immune system or stimulation of a local or systemic effector system. Major inflammatory diseases include gastrointestinal diseases such as gastritis, inflammatory enteritis, etc., oral diseases such as periodontitis, etc., respiratory diseases such as asthma, chronic obstructive pulmonary disease (COPD), rhinitis, etc., skin diseases such as atopic dermatitis, hair loss and psoriasis, etc., arthritis such as degenerative arthritis, rheumatoid arthritis, etc., and metabolic diseases such as obesity, diabetes, cirrhosis, etc. In addition, various studies have reported results that sustained inflammation can cause cancer (Cancers 2014, 6, 926-957).

The number of microorganisms that are symbiotic with the human body is 100 trillion, which is 10-fold larger than the number of human cells, and it has been known that the number of microbial genes is over 100-fold larger than that of the human genes. A microbiota or microbiome refers to the microbial community including bacteria, archaea and eukaryotes, present in a given habitat, and the intestinal microbiota plays an important role in the physiological phenomenon of a human, and has been known to have great effect on human health and diseases through the interaction with human cells.

Bacteria and archaea which are symbiotic with a human body secrete nanometer-scale vesicles (nanovesicles) for the exchange of genetic or protein information with other cells. The mucous membrane forms a physical defense membrane through which particles having a size of 200 nanometers (nm) or more cannot pass, and while bacteria symbiotic with the mucous membrane cannot pass through the mucous membrane, since bacteria-derived nanovesicles are 100 nm or less in size, they relatively freely pass through epithelial cells via the mucous membrane and thus are absorbed to a human body. Pathogenic bacteria-derived vesicles, which are absorbed in the human body, have been identified as a factor critical for the cause of an inflammatory disease, for example, an inflammatory dermal disease such as atopic dermatitis, an inflammatory respiratory disease such as chronic rhinitis, asthma or COPD, or an inflammatory intestinal disease such as ulcerative colitis or Crohn's disease. In addition, it has been recently revealed that the pathogenic bacteria-derived vesicles are also closely related to the occurrence of a metabolic disease such as diabetes or obesity, or solid cancer such as lung cancer, gastric cancer or colon cancer, and have received attention. However, there is no case of diagnosing cancer, a chronic inflammatory disease or a metabolic disease by quantifying vesicles derived from bacteria of the genus *Bacillus* in a clinical sample yet.

The genus *Bacillus* bacteria are Gram-positive bacilli included in the phylum Firmicutes, which can survive for a long period of time since they grow in an anaerobic environment as well as an aerobic environment, and form spores in a stress situation. Among bacteria of the genus *Bacillus*, *Bacillus subtilis* is a Gram-positive *bacillus* which may be grown in a non-pathogenic, aerobic environment, and widely distributed in nature such as dry grass, sewage, soil and dust as well as in air. In addition, *Bacillus subtilis* natto, which is a *Bacillus subtilis* subtype, may be grown even in an anaerobic environment, and since it is inhabited by being attached to rice straws, in the production of cheonggukjang, when beans are heated up to approximately 40° C. along with rice straws pinning in the beans in an anaerobic condition, *Bacillus subtilis* natto is grown in large quantities. Cheonggukjang is a Korean traditional food made by fermenting soybeans, and similar to Japanese natto. While doenjang takes several months of fermentation for eating, cheonggukjang is edible within 2 to 3 days through fermentation. In other words, cheonggukjang can be made within the shortest period of time among fermented soybean pastes. Cheonggukjang made through natural fermentation is made by soaking soybeans in hot water for 10 to 20 hours, boiling the soaked soybeans with additional water to be sufficiently cooked, and incubating the soybeans for fermentation. When straws are uniformly placed on a container, and the boiled soybeans are poured thereon, cooled to 60° C. and placed in a warm place while being covered with a blanket or a comforter to maintain the temperature to 45° C., *Bacillus subtilis* natto is generated to ferment the soybeans to a fermented product.

General compositions which are used to treat or prevent a chronic inflammatory disease are largely classified into steroid compositions and non-steroid compositions, and in many cases, most of them are often accompanied by various side effects. In addition, in terms of the cause of an inflammatory disease such as rheumatoid arthritis, hair loss or inflammatory enteritis, the importance of TNF-α has attracted attention, and as a therapeutic agent for rheumatoid arthritis, a TNF-α inhibitor is in the limelight. However, there is no case that gene quantification in vesicles secreted from bacteria of the genus *Bacillus* or *Bacillus subtilis* is used to diagnose cancer, a chronic inflammatory disease or a metabolic disease, or the vesicles are used to prevent or treat an inflammatory disease.

DISCLOSURE

Technical Problem

The inventors had intensively studied to solve the existing problems, and confirmed through metagenomic analysis for bacteria-derived nanovesicles present in a human sample that, compared with a normal person, in a sample obtained from a patient with solid cancer such as liver cancer, bladder cancer, breast cancer or ovarian cancer, a chronic inflammatory disease such as asthma or atopic dermatitis, or a metabolic disease such as diabetes or liver cirrhosis, a content of vesicles derived from bacteria of the genus *Bacillus* is considerably reduced. The inventors confirmed, as a result of that evaluation of therapeutic efficacy, that vesicles isolated from in vitro cultured *Bacillus* bacteria, particularly, *Bacillus subtilis*, showed an excellent anti-inflammatory effect, thereby completing the present invention.

Therefore, the present invention is directed to providing a method of providing information for diagnosis of cancer, a chronic inflammatory disease and a metabolic disease.

The present invention is also directed to providing a composition for preventing or treating cancer, a chronic inflammatory disease and a metabolic disease, which includes vesicles derived from bacteria of the genus *Bacillus* as an active ingredient.

However, technical problems to be solved in the present invention are not limited to the above-described problems, and other problems which are not described herein will be fully understood by those of ordinary skill in the art from the following descriptions.

Technical Solution

To attain the objects of the present invention, the present invention provides a method of providing information for diagnosis of cancer, a chronic inflammatory disease and a metabolic disease, which includes the following steps:
   (a) extracting DNA from vesicles isolated from samples obtained from a normal person and a subject;
   (b) obtaining a PCR product by performing PCR on the extracted DNA using a primer pair for detecting vesicles derived from bacteria of the genus *Bacillus*, present in a 16S rDNA sequence; and
   (c) determining as cancer, an inflammatory disease or a metabolic disease through quantitative analysis of the PCR product when a content of vesicles derived from bacteria of the genus *Bacillus* is lower than that of a normal person.

In one exemplary embodiment of the present invention, the cancer may be liver cancer, bladder cancer, breast cancer, or ovarian cancer.

In another exemplary embodiment of the present invention, the chronic inflammatory disease may be asthma, chronic hepatitis or atopic dermatitis.

In still another exemplary embodiment of the present invention, the metabolic disease may be diabetes or cirrhosis.

In yet another exemplary embodiment of the present invention, the sample obtained from the patient may be a blood, urine or stool sample.

The present invention also provides a pharmaceutical composition for preventing or treating cancer, an inflammatory disease or a metabolic disease, which includes vesicles derived from bacteria of the genus *Bacillus* as an active ingredient.

In one exemplary embodiment of the present invention, the present invention provides a health functional food composition for alleviating cancer, an inflammatory disease or a metabolic disease, which includes vesicles derived from bacteria of the genus *Bacillus* as an active ingredient.

In another exemplary embodiment of the present invention, the present invention provides an inhalant composition for preventing or treating cancer, an inflammatory disease or a metabolic disease, which includes vesicles derived from bacteria of the genus *Bacillus* as an active ingredient.

In still another exemplary embodiment of the present invention, a cosmetic composition for alleviating an inflammatory disease, which includes vesicles derived from bacteria of the genus *Bacillus* as an active ingredient.

In yet another exemplary embodiment of the present invention, the vesicles derived from bacteria of the genus *Bacillus* may be *Bacillus subtilis*-derived vesicles.

In yet another exemplary embodiment of the present invention, the *Bacillus subtilis*-derived vesicles may be *Bacillus subtilis* natto-derived vesicles.

In yet another exemplary embodiment of the present invention, the cancer may be selected from the group consisting of liver cancer, bladder cancer, breast cancer and ovarian cancer; the inflammatory disease may be selected from the group consisting of asthma, chronic hepatitis, hair loss, rheumatoid arthritis, inflammatory enteritis and atopic dermatitis; and the metabolic disease may be diabetes or cirrhosis.

In yet another exemplary embodiment of the present invention, the inflammatory disease may be one or more diseases selected from the group consisting of rheumatoid arthritis, hair loss and inflammatory enteritis, in which an inflammatory cytokine such as IL-6 or TNF-α is involved as the cause thereof.

In yet another exemplary embodiment of the present invention, the vesicles may have an average diameter of 10 to 200 nm.

In yet another exemplary embodiment of the present invention, the vesicles may be naturally or artificially secreted from bacteria of the genus *Bacillus*.

In yet another exemplary embodiment of the present invention, the vesicles may be isolated from a culture solution of bacteria of the genus *Bacillus*.

The present invention also provides a method of preventing or treating cancer, an inflammatory disease or a metabolic disease, which includes administering a pharmaceutical composition including vesicles derived from bacteria of the genus *Bacillus* of the present invention as an active ingredient to a subject.

The present invention also provides a use of vesicles derived from bacteria of the genus *Bacillus* for preventing or treating an inflammatory disease.

Advantageous Effects

The inventors confirmed that intestinal bacteria are not absorbed into a body, but bacteria-derived vesicles are absorbed into the body and systemically dispersed, and then excreted through the kidneys, the liver or the lungs, and also confirmed through metagenomic analysis for bacteria-derived vesicles present in the blood, urine or feces of a patient that vesicles derived from bacteria of the genus *Bacillus*, present in the blood of a patient with solid cancer such as liver cancer, bladder cancer, breast cancer or ovarian cancer, a chronic inflammatory disease such as asthma or atopic dermatitis, or a metabolic disease such as diabetes or liver cirrhosis are significantly less than those of a normal person.

In addition, when a *Bacillus subtilis* standard strain, which is one species of bacteria of the genus *Proteus*, and *Bacillus subtilis* natto, which is a *Bacillus subtilis* subtype, are cultured in vitro to isolate vesicles, and the vesicles are administered to inflammatory cells in vitro, it was observed that the secretion of inflammatory mediators due to pathogenic vesicles is significantly inhibited, showing that the vesicles derived from bacteria of the genus *Bacillus* according to the present invention can be effectively used for a method of diagnosing or predicting cancer, a chronic inflammatory disease or a metabolic disease, and a food, inhalant, cosmetic or pharmaceutical composition for preventing or treating cancer, a chronic inflammatory disease or a metabolic disease.

DESCRIPTION OF DRAWINGS

FIG. 1A shows a set of images representing distribution patterns of bacteria and vesicles by time after cells and cell-derived vesicles (EV) were orally administered to mice.

FIG. 1B shows a set of images which evaluate distribution patterns of cells and vesicles in a body by extracting the blood, kidneys, liver and various organs at 12 hours after oral administration.

FIG. 2 is a diagram which schematically illustrates a metagenomic analysis method for cell-derived vesicles originating from a human-derived sample.

FIG. 3 shows a result of comparing the distribution of vesicles derived from bacteria of the genus *Bacillus* after metagenomic analysis is performed on bacteria-derived vesicles present in the blood of a liver cancer patient and a normal person.

FIG. 4 shows a result of comparing the distribution of vesicles derived from bacteria of the genus *Bacillus* after metagenomic analysis is performed on bacteria-derived vesicles present in the blood of a bladder cancer patient and a normal person.

FIG. 5 shows a result of comparing the distribution of vesicles derived from bacteria of the genus *Bacillus* after metagenomic analysis is performed on bacteria-derived vesicles present in the blood of a breast cancer patient and a normal person.

FIG. 6 shows a result of comparing the distribution of vesicles derived from bacteria of the genus *Bacillus* after metagenomic analysis is performed on bacteria-derived vesicles present in the blood of an ovarian cancer patient and a normal person.

FIG. 7 shows a result of comparing the distribution of vesicles derived from bacteria of the genus *Bacillus* after metagenomic analysis is performed on bacteria-derived vesicles present in the blood of an asthma patient and a normal person.

FIG. 8 shows a result of comparing the distribution of vesicles derived from bacteria of the genus *Bacillus* after metagenomic analysis is performed on bacteria-derived vesicles present in the blood of an atopic dermatitis patient and a normal person.

FIG. 9 shows a result of comparing the distribution of vesicles derived from bacteria of the genus *Bacillus* after metagenomic analysis is performed on bacteria-derived vesicles present in the blood of a diabetes patient and a normal person.

FIG. 10 shows a result of comparing the distribution of vesicles derived from bacteria of the genus *Bacillus* after metagenomic analysis is performed on bacteria-derived vesicles present in the blood of a cirrhosis patient and a normal person.

FIG. 11 shows a result of comparing the distribution of vesicles derived from bacteria of the genus *Escherichia* after metagenomic analysis is performed on bacteria-derived vesicles present in the blood of a diabetes patient and a normal person.

FIG. 12A shows a result of measuring the morphology and size of *Bacillus subtilis*-derived vesicles isolated from a *Bacillus subtilis* culture solution by ultracentrifugation through electron microscopy.

FIG. 12B shows a result of measuring the morphology and size of *Bacillus subtilis*-derived vesicles isolated from a *Bacillus subtilis* culture solution by ultracentrifugation through dynamic light scattering FIG. 13A shows a result of comparing the secretion of inflammatory mediators after a macrophage Raw 264.7 cell line is treated with *Escherichia coli*-derived vesicles (*E. coli* EV), which is a causative factor of cancer, an inflammatory disease or a metabolic disease, as a positive control, *Bacillus subtilis* standard strain-derived vesicles (*Bacillus subtilis* EV) and *Bacillus subtilis* natto-derived vesicles (*Bacillus subtilis* natto EV) at various concentrations, and a concentration of IL-6, which is an inflammatory mediator, is measured through ELISA [NC: negative control (PBS), EV: extracellular vesicle].

FIG. 13B shows a result of comparing a degree of secreting inflammatory mediators after a macrophage Raw 264.7 cell line is treated with *E. coli* EV, which is a causative factor of cancer, an inflammatory disease or a metabolic disease, as a positive control, *Bacillus subtilis* standard strain-derived vesicles (*Bacillus subtilis* EV) and *Bacillus subtilis* natto-derived vesicles (*Bacillus subtilis* natto EV) at various concentrations, and a concentration of TNF-α, which is an inflammatory mediator, is measured through ELISA [NC: negative control (PBS), EV: extracellular vesicle].

FIG. 14A shows a result of evaluating anti-inflammatory effects of vesicles derived from a *Bacillus subtilis* standard strain and a *Bacillus subtilis* natto strain after a macrophage Raw 264.7 cell line is pre-treated with *Lactobacillus plantarum*-derived vesicles (*L. plantarum* EV) as a control drug, *Bacillus subtilis* standard strain-derived vesicles (*Bacillus subtilis* EV) and *Bacillus subtilis* natto-derived vesicles (*Bacillus subtilis* natto EV), 12 hours after the pre-treatment, *E. coli*-derived vesicles as a causative factor of inflammation are treated, and an IL-6 concentration is measured through ELISA [NC: negative control (PBS), PC: positive control, EV: extracellular vesicle].

FIG. 14B shows a result of evaluating anti-inflammatory effects of vesicles derived from a *Bacillus subtilis* standard strain and a *Bacillus subtilis* natto strain after a macrophage Raw 264.7 cell line is pre-treated with *Lactobacillus plantarum*-derived vesicles (*L. plantarum* EV) as a control drug, *Bacillus subtilis* standard strain-derived vesicles (*Bacillus subtilis* EV) and *Bacillus subtilis* natto-derived vesicles (*Bacillus subtilis* natto EV), 12 hours after the pre-treatment, *E. coli*-derived vesicles as a causative factor of inflammation are treated, and a TNF-α concentration is measured through ELISA [NC: negative control (PBS), PC: positive control, EV: extracellular vesicle].

MODES OF THE INVENTION

The present invention relates to vesicles derived from bacteria of the genus *Bacillus* and a use thereof.

The inventors confirmed that, compared with a normal person, in a sample obtained from a patient with solid cancer such as liver cancer, bladder cancer, breast cancer or ovarian cancer, a chronic inflammatory disease such as asthma or atopic dermatitis, or a metabolic disease such as diabetes or liver cirrhosis, a content of vesicles derived from bacteria of the genus *Bacillus* is considerably reduced through metagenomic analysis. In addition, when vesicles derived from a *Bacillus subtilis* standard strain and a *Bacillus subtilis* strain, *Bacillus subtilis* natto, which are included in bacteria of the genus *Bacillus*, are isolated and administered to inflammatory cells, it was confirmed that an inflammatory response against *E. coli*-derived vesicles, which are pathogenic vesicles, is effectively inhibited, and therefore, the present invention was completed.

In one aspect, the present invention provides a method of providing information for diagnosis of cancer, a chronic inflammatory disease or a metabolic disease, which includes the following steps:
(a) extracting DNA from vesicles isolated from samples obtained from a normal person and a subject;
(b) obtaining a PCR product by performing PCR on the extracted DNA using a primer pair for detecting vesicles derived from bacteria of the genus *Bacillus*, present in a 16S rDNA sequence; and
(c) determining as cancer, an inflammatory disease or a metabolic disease through quantitative analysis of the PCR product when a content of vesicles derived from bacteria of the genus *Bacillus* is lower than those of a normal person.

In addition, the inventors confirmed, through metagenomic analysis, that, compared with a normal person, in a sample obtained from a patient with diabetes, a content of vesicles derived from bacteria of the genus *Escherichia* is dramatically increased, and therefore the present invention provides a method of providing information for diagnosis of diabetes, which includes the following steps:
(a) extracting DNA from vesicles isolated from samples obtained from a normal person and a subject;
(b) obtaining a PCR product by performing PCR on the extracted DNA using a primer pair for detecting vesicles derived from bacteria of the genus *Escherichia*, present in a 16S rDNA sequence; and
(c) determining as diabetes through quantitative analysis of the PCR product when a content of vesicles derived from bacteria of the genus *Escherichia* is higher than that of a normal person.

The term "diagnosis" used herein refers to the judgment of the actual condition of the patient's disease in all aspects. The contents of the judgment include the name of a disease, the cause of a disease, the type of a disease, severity, detailed aspects of the conditions of a disease, the presence or absence of complications, and prognosis. The diagnosis of the present invention is to judge the occurrence of a disease such as cancer, a chronic inflammatory disease or a metabolic disease and the level of disease.

In another aspect, the present invention provides a food, cosmetic, inhalant or pharmaceutical composition for preventing or treating cancer, a chronic inflammatory disease, or a metabolic disease, which includes vesicles derived from bacteria of the genus *Bacillus* as an active ingredient.

The term "prevention" used herein refers to all actions inhibiting or delaying cancer, a chronic inflammatory disease, or a metabolic disease by administration of the pharmaceutical composition according to the present invention.

The term "treatment" used herein refers to all actions involved in alleviating or beneficially changing symptoms of cancer, a chronic inflammatory disease, or a metabolic disease by administration of the food, cosmetic, inhalant or pharmaceutical composition according to the present invention.

The vesicles derived from bacteria of the genus *Bacillus* of the present invention may be isolated from a culture solution of bacteria of the genus *Bacillus* or fermented food made using bacteria of the genus *Bacillus*, and preferably, isolated from a culture solution of *Bacillus subtilis* or *Bacillus subtilis* natto or fermented food made using *Bacillus subtilis* or *Bacillus subtilis* natto, and naturally or artificially secreted from *Bacillus subtilis* or *Bacillus subtilis* natto, but the present invention is not limited thereto.

A method of isolating the culture solution or fermented food of the bacteria of the genus *Bacillus* of the present invention is not particularly limited as long as the culture solution or fermented food includes vesicles. For example, the vesicles may be isolated using a method such as centrifugation, ultracentrifugation, filtration by a filter, gel filtration chromatography, free-flow electrophoresis or capillary electrophoresis, and the method may further include washing for removing cell debris, and concentration of the collected vesicles.

In the present invention, the vesicles isolated by the above-described method preferably have an average diameter of 10 to 1000 nm, and more preferably, 40 to 100 nm, but the present invention is not limited thereto.

The pharmaceutical composition according to the present invention may include vesicles derived from bacteria of the genus *Bacillus* as an active ingredient, and a pharmaceutically acceptable carrier. The pharmaceutically acceptable carrier is conventionally used in preparation, and includes saline, distilled water, Ringer's solution, buffered saline, a cyclodextrin solution, a dextrose solution, a maltodextrin solution, glycerol, ethanol, liposomes, etc., but the present invention is not limited thereto. If needed, other conventionally used additives such as an antioxidant and a buffer may be further included. In addition, an injectable preparation such as an aqueous solution, a suspension or an emulsion, a pill, a capsule, a granule or a tablet may be formulated by additionally adding a diluent, a dispersant, a surfactant, a binder, a lubricant, etc. Suitable pharmaceutically acceptable carriers and their formulations may be formulated according to each component using a method disclosed in the Remington's Pharmaceutical Science. The pharmaceutical composition of the present invention is not limited in dosage form, and thus may be formulated as an injection, an inhalant, or an external preparation for skin.

The pharmaceutical composition of the present invention may be administered orally or non-orally (e.g., intravenously, subcutaneously, intraperitoneally or locally) depending on a desired method, and a dose of the pharmaceutical composition may vary depending on the condition and body weight of a patient, the severity of a disease, a drug type, an administration route and time, and may be suitably selected by one of ordinary skill in the art.

The pharmaceutical composition of the present invention is administered at a pharmaceutically effective amount. The "pharmaceutically effective amount" used herein refers to an amount sufficient for treating a disease at a reasonable benefit/risk ratio applicable for medical treatment, and an effective dosage may be determined by parameters including a type of a patient's disease, severity, drug activity, sensitivity to a drug, administration time, an administration route and an excretion rate, the duration of treatment and drugs simultaneously used, and other parameters well known in medical fields. The pharmaceutical composition of the present invention may be administered separately or in combination with other therapeutic agents, and may be sequentially or simultaneously administered with a conventional therapeutic agent, or administered in a single or multiple dose(s). In consideration of all of the above-mentioned parameters, it is important to achieve the maximum effect with the minimum dose without a side effect, and such a dose may be easily determined by one of ordinary skill in the art.

Specifically, an effective amount of the composition according to the present invention may be determined by a patient's age, sex or body weight. Generally, the composition may be administered at a dose of 0.001 to 150 mg, and preferably, 0.01 to 100 mg, per kg of body weight daily or every second day, or with a single or three equal portions of the daily dose. However, since the dose may vary according to an administration route, the severity of obesity, a sex, a body weight, an age, etc., the dose does not limit the scope of the present invention in any way.

In still another aspect of the present invention, the present invention provides a health functional food composition for alleviating cancer, an inflammatory disease or a metabolic disease, which includes vesicles derived from bacteria of the genus *Bacillus* as an active ingredient.

The term "alleviation" used herein refers to all types of actions that at least reduce parameters related to a condition to be treated, for example, a degree of a symptom.

In a health functional food composition of the present invention, an active ingredient may be added to food alone or in combination with other food or food component, and may be suitably used according to a conventional method. A mixing amount of the active ingredient may be suitably determined by a purpose of used thereof (for prevention or alleviation). Generally, in food or beverage production, the composition of the present invention is added at 15 wt % or less, and preferably, 10 wt % or less with respect to the raw materials. However, in the case of long-term intake for health and sanitary or health control, the amount may be below the above-mentioned range.

The health functional food composition of the present invention has no specific limitation in components, except the active ingredient as an essential component at a predetermined proportion, and may include various flavors or natural carbohydrates as additional components like a general beverage. Examples of the above-described natural carbohydrates include monosaccharides such as glucose, fructose, etc.; disaccharides such as maltose, sucrose, etc.; and polysaccharides such as general sugars such as dextrin, cyclodextrin, etc., and sugar alcohols such as xylitol, sorbitol, erythritol, etc. Other than the above-described components, as flavoring agents, natural flavoring agents (thaumatin, a *stevia* extract (e.g., rebaudioside A, glycyrrhizin), etc.) and synthetic flavoring agents (saccharin, aspartame, etc.) may be advantageously used. The proportion of the natural carbohydrate may be suitably determined by a choice of those of ordinary skill in the art.

Other than the above-described components, the health functional food composition of the present invention may contain various nutrients, vitamins, minerals (electrolytes), flavoring agents such as synthetic and natural flavoring agents, coloring agents, thickening agents (cheese, chocolate, etc.), pectic acid and a salt thereof, alginic acid and a salt thereof, an organic acid, a protective colloid thickening agent, a pH adjuster, a stabilizer, a preservative, glycerin, an alcohol, and a carbonating agent used in a carbonated beverage. These components may be used independently or in combination thereof. The proportions of these additives may be suitably selected by those of ordinary skill in the art.

In yet another aspect, the present invention provides an inhalant composition for preventing or treating an inflammatory disease, which includes vesicles derived from bacteria of the genus *Bacillus* as an active ingredient.

In the inhalant composition of the present invention, the active ingredient may be added to an inhalant alone or in combination with other components, and may be suitably used by a conventional method. A mixing amount of the active ingredient may be suitably determined by a purpose of use thereof (for prevention or treatment).

In yet another aspect, the present invention provides a cosmetic composition for alleviating an inflammatory disease or hair loss, which includes vesicles derived from bacteria of the genus *Bacillus* as an active ingredient.

The cosmetic composition of the present invention may include components conventionally used in a cosmetic composition as well as vesicles derived from bacteria of the genus *Bacillus*, and the components conventionally used in a cosmetic composition may include a conventional excipient such as an antioxidant, a stabilizer, a solubilizer, a vitamin, a pigment and a flavor, and a carrier.

In addition, the composition of the present invention may further include a conventionally used organic UV blocking agent which is mixed by being reacted with the vesicles derived from bacteria of the genus *Bacillus* so long as it does not impair a skin protection effect. The organic UV blocking agent may be one or more selected from the group consisting of glyceryl PABA, drometrizole trisiloxane, drometrizol, digalloyl triolelate, disodium phenyl dibenzimidazole tetrasulfonate, diethylhexylbutamidotriazone, diethylaminohydroxybenzoylhexylbenzoate, DEA-methoxycinnamate, a mixture of lawsone and dihydroxyacetone, methylenebisbenzotriazolyltetramethylbutylphenol, 4-methylbenzylidene camphor, menthyl anthranilate, benzophenone-3(oxybenzone), benzophenone-4, benzophenone-8 (dioxybenzone), butyl methoxydibenzoylmethane, bisethylhexyloxyphenolmethoxyphenyltriazine, cinoxate, ethyl dihydroxypropyl PAVA, octocrylene, ethylhexyl dimethyl PABA, ethylhexyl methoxy cinnamate, ethylhexyl salicylate, ethylhexyltriazone, isoamyl-p-methoxycinnamate, polysilicone-15 (dimethicodiethyl benzal malonate), terephthalylidene dicamphor sulfonic acid and a salt thereof, TEA-salicylate, and aminobenzoic acid (PAVA).

As a product to which the cosmetic composition of the present invention can be added, for example, cosmetics such as an astringent toner, a softening toner, a nourishing toner, various types of creams, essences, packs and foundations, and a cleanser, soap, a treatment or a cosmetic solution may be used. Specific examples of the cosmetic composition of the present invention include a skin lotion, a skin softener, a skin toner, an astringent, a lotion, a milk lotion, a moisturizer lotion, a nourishing lotion, a massage cream, a nourishing cream, a moisturizer cream, a hand cream, an essence, a nourishing essence, a pack, soap, a shampoo, a cleansing foam, a cleansing lotion, a cleansing cream, a body lotion, a body cleanser, an emulsion, a lipstick, a makeup base, a foundation, a pressed powder, a loose powder, and an eyeshadow.

According to an exemplary embodiment of the present invention, a content of the vesicles derived from bacteria of the genus *Bacillus* of the present invention may be 0.00001 to 30 wt % with respect to a total weight of the composition, preferably 0.5 to 20 wt %, and more preferably 1.0 to 10 wt %. When the content of the vesicles derived from bacteria of the genus *Bacillus* is less than 0.00001 wt %, a UV absorption effect is greatly reduced, and when the content of the vesicles derived from bacteria of the genus *Bacillus* is more than 30 wt %, skin irritation may occur, and there may be a problem in dosage form.

In yet another aspect, the present invention provides a method of preventing or treating cancer, an inflammatory disease or a metabolic disease, which includes administering a composition including vesicles derived from bacteria of the genus *Bacillus* as an active ingredient to a subject.

The term "subject" used herein refers to a subject in need of treatment, and more specifically, a mammal such as a human, or a non-human primate, a mouse, a rat, a dog, a cat, a horse, and a cow.

The cancer used herein, which is a disease subjected to diagnosis, indicates a malignant tumor which infiltrates into peripheral tissue, is grown rapidly and is diffused or transited to each part of a body, thereby becoming life-threatening. A cell, which is the smallest unit in a body, is normally divided and grown by the regulatory function thereof, dies by itself when it nears the end of its lifespan or is damaged, thereby maintaining an overall balance in number. However, if there is a problem in the regulation of these cells due to various reasons, abnormal cells which should normally die are excessively proliferated, they infiltrate into peripheral tissue and organ, thereby forming a mass, and an existing structure is destroyed or transformed. In the present invention, cancer is preferably liver cancer, bladder cancer, breast cancer or ovarian cancer, but the present invention is not limited thereto.

The term "inflammatory disease" used herein refers to a disease caused by an inflammation response in a mammalian body, and representative examples of the inflammatory disease include a respiratory inflammatory disease such as asthma, chronic obstructive pulmonary disease or rhinitis; a skin inflammatory disease such as atopic dermatitis, psoriasis, acne, contact dermatitis or hair loss; a digestive inflammatory disease such as gastritis, digestive ulcers or inflammatory enteritis; vaginitis; arthritis such as osteoarthritis or rheumatoid arthritis; and a complication thereof. In addition, the inflammatory disease may include, as well as general inflammatory diseases, cancer associated with an inflammatory response, for example, breast cancer, ovarian cancer, bladder cancer or liver cancer. In addition, the inflammatory disease includes, as well as a general inflammatory disease, a metabolic disease associated with an inflammatory response, for example, diabetes, obesity, or cirrhosis. In the present invention, the chronic inflammatory disease preferably includes asthma, chronic hepatitis, hair loss, or atopic dermatitis, but the present invention is not limited thereto.

The term "metabolic disease" used herein refers to a disease which has metabolic disorder-induced complications occurring in various organs in a mammalian body. For example, a carbohydrate metabolic disorder such as diabetes and a complication thereof include cirrhosis, and in the present invention, the metabolic disease preferably includes diabetes and cirrhosis, but the present invention is not limited thereto.

The term "nanovesicle or vesicle" used herein refers to a nano-scale membrane-shaped structure secreted from various bacteria. A Gram-negative bacteria-derived vesicle or outer membrane vesicle (OMV) has a toxic protein, bacterial DNA and RNA, as well as a lipopolysaccharide, and a gram-positive bacteria-derived vesicle also has peptidoglycan and lipoteichoic acid, which are bacterial cell wall components, as well as a protein and a nucleic acid. In the present invention, the nanovesicle or vesicle is naturally secreted and artificially produced from a bacterium of the genus *Bacillus*, and has a spherical shape with an average diameter of 10 to 200 nm.

The term "metagenome" used herein, also referred to as "microbiome," means the total of genomes present in all viruses, bacteria, fungi, etc. reside in an isolated region such as soil, an animal intestine, etc., and is used as the concept of a genomic material for explaining that many microorganisms are identified at one time using a sequencer to usually analyze microorganisms which are not able to be cultured. Particularly, the metagenome does not refer to a genome of one species but refers to a mixed genome of all species in a single environmental unit. This term originates from the viewpoint that, when one species is defined in a process in which biology is advanced into omics, various species as well as an existing one species functionally interact with each other to form a complete species. Technically, the metagenome is a subject for a technique of identifying all species in one environment and defining interactions and metabolic actions by analyzing all of DNA and RNA regardless of species through rapid sequencing.

In the present invention, the bacteria-derived nanovesicles may be isolated from a culture solution containing bacteria using one or more methods selected from the group consisting of centrifugation, ultracentrifugation, extrusion, ultrasonication, cell lysis, homogenization, freezing-thawing, electroporation, mechanical decomposition, treatment with a chemical, filtration by a filter, gel filtration chromatography, free-flow electrophoresis, and capillary electrophoresis. In addition, the above-mentioned methods may further include washing for removing cell debris, and concentration of the collected vesicles.

In an exemplary embodiment of the present invention, as a result of orally administering bacteria or bacteria-derived vesicles to mice to evaluate body absorption, distribution and excretion patterns of bacteria and vesicles thereof, it was confirmed that bacteria are not absorbed through an intestinal mucous membrane, but vesicles are absorbed within 5 minutes after administration to be distributed into the whole body, and excreted through the kidneys, liver, etc. (refer to Example 1).

In one exemplary embodiment of the present invention, using vesicles isolated from the blood of each of patients with liver cancer, bladder cancer, breast cancer and ovarian cancer, and normal persons matching the age and sex of the cancer patients, bacterial metagenomic analysis was performed. The analysis result showed that, compared with a normal sample, the vesicles derived from bacteria of the genus *Bacillus* are significantly reduced in the samples of the liver cancer, bladder cancer, breast cancer and ovarian cancer patients (refer to Examples 3, 4, 5 and 6).

In another exemplary embodiment of the present invention, bacterial metagenomic analysis was performed using vesicles isolated from samples of patients with asthma and atopic dermatitis and normal persons matching the patients' age and sex. The analysis result showed that, compared with the samples of the normal persons, in the samples of the patients with asthma and atopic dermatitis, the vesicles derived from the bacteria of the genus *Bacillus* are significantly reduced (refer to Examples 7 and 8).

In still another exemplary embodiment of the present invention, bacterial metagenomic analysis was performed using vesicles isolated from samples of patients with diabetes and cirrhosis, and normal persons matching the patients' age and sex. The analysis result showed that, compared with the samples of the normal persons, in the samples of the patients with diabetes and cirrhosis, the vesicles derived from the bacteria of the genus *Bacillus* are significantly reduced (refer to Examples 9 and 10).

In yet another exemplary embodiment of the present invention, bacterial metagenome analysis was performed using vesicles isolated from samples of diabetic patients and normal persons matching the patients' age and sex. The analysis result showed that, compared with the samples of the normal persons, in the samples of the diabetic patients, the vesicles derived from bacteria of the genus *Escherichia* are significantly increased (refer to Example 11).

In yet another exemplary embodiment of the present invention, as a result of an intensive study for evaluating whether vesicles derived from bacteria of the genus *Bacillus* inhibit an inflammatory response by a causative factor of cancer, a chronic inflammatory disease or a metabolic disease, it was observed that, in the case of *Bacillus subtilis* (standard strain)-derived vesicles and vesicles derived from *Bacillus subtilis* natto, which is a *Bacillus subtilis* subtype, compared with *E. coli*-derived vesicles, there was almost no inflammation-causing effect, and it was observed that when the *Bacillus subtilis* or *Bacillus subtilis* natto-derived vesicles were pre-treated, the inflammatory response caused by the vesicles derived from *E. coli*, which is the pathogenic causative factor, was efficiently inhibited, thereby completing the present invention (refer to Examples 13 and 14).

Hereinafter, to help in understanding the present invention, exemplary examples will be suggested. However, the following examples are merely provided to more easily understand the present invention, and not to limit the present invention.

EXAMPLES

Example 1. Analysis of Body Absorption, Differentiation and Excretion Patterns of Bacteria and Bacteria-Derived Vesicles To evaluate whether bacteria of the genus *Bacillus* and vesicles derived therefrom are absorbed into the whole body through the gastrointestinal tract, an experiment was performed by the following method. Bacteria or bacteria-derived vesicles, which were labeled with fluorescence, were administered into the mouse stomach through the gastrointestinal tract at a dose of 50 μg, and after 0 minute, 5 minutes, 3 hours, 6 hours or 12 hours, fluorescence was measured. As a result of observing the full images of mice, the bacteria were not absorbed into the whole body, but the bacteria-derived vesicles were absorbed into the whole body at 5 minutes after administration, and strong fluorescence was observed in the liver and the kidneys at 30 minutes after administration, indicating excretion of the vesicles into the liver and the urinary system. In addition, it can be seen that the vesicles are present in the body until 12 hours after administration (refer to Example 1A).

To evaluate a pattern of infiltrating the bacteria or bacteria-derived vesicles into various organs after being absorbed into the whole body, 50 μg of the fluorescence-labeled bacteria and bacteria-derived vesicles were administered by the above-described method, and 12 hours after administration, the blood, heart, liver, kidneys, spleen, fat, and muscle were extracted for sampling. As a result of observing the fluorescence in the sampled tissues, it can be seen that the bacteria-derived nanovesicles were distributed into the blood, heart, lung, liver, kidneys, spleen, fat and muscle, but the bacteria were not absorbed (refer to Example 1B).

Example 2. Metagenomic Analysis of Bacteria-Derived Vesicles in Clinical Samples A clinical sample such as blood was first added to a 10 ml tube and subjected to centrifugation (3,500×g, 10 min, 4° C.) to precipitate a suspended material, and then only the supernatant was transferred to a new 10 ml tube. After bacteria and the cell debris were removed using a 0.22-μm filter, the resulting product was transferred to a Centriprep tube (centrifugal filters 50 kD) and subjected to centrifugation at 1500×g and 4° C. for 15 minutes to discard materials smaller than 50 kD, followed by concentration of the resulting product up to 10 ml. Again, the bacteria and the cell debris were removed using a 0.22-μm filter, vesicles were isolated and dissolved in phosphate-buffered saline (PBS).

100 μL of the vesicles isolated by the above-described method were boiled at 100° C. to release internal DNA out of a lipid, and then cooled on ice for 5 minutes. In addition, to remove a remaining suspended material, the vesicles were subjected to centrifugation at 10,000×g and 4° C. for 30 minutes, followed by collecting a supernatant. Moreover, a DNA level was quantified by NanoDrop. Afterward, to confirm whether bacterial DNA is present in the extracted DNA, PCR was performed using the 16s rDNA primers shown in Table 1 below to confirm that bacterial genes are present in the extracted gene.

TABLE 1

| Primer | | Sequence | SEQ. ID. NO: |
|---|---|---|---|
| 16S rDNA | 16S_V3_F | 5'-TCGTCGGCAGCGTCAGATG TGTATAAGAGACAGCCTACGGG NGGCWGCAG-3' | 1 |
| | 16S_V4_R | 5'-GTCTCGTGGGCTCGGAGAT GTGTATAAGAGACAGGACTACH VGGGTATCTAATCC-3 | 2 |

The DNA extracted by the above-described method was amplified using the 16S rDNA primers and subjected to sequencing (Illumina MiSeq sequencer), and the sequencing result was output to a Standard Flowgram Format (SFF) file and the SFF file was converted into a sequence file (.fasta) and a nucleotide quality score file using GS FLX software (v2.9), followed by evaluating the reliability of the reads, a site having the mean base call accuracy of the window (20 bps) of less than 99% (Phred score <20) was removed. To analyze Operational Taxonomy Units (OTUs), clustering was performed according to sequence similarity using UCLUST and USEARCH, the clustering was performed based on 94, 90, 85, 80 and 75% sequence similarities of the genus, family, order, class and phylum, respectively, the OTUs were classified into taxonomic levels (phylum, class, order, family and genus), and bacteria having 97% or more sequence similarity were profiled at the genus level using the 16S RNA sequence database (108,453 sequences) obtained from BLASTN or GreenGenes (QIIME).

Example 3. Confirmation of Decrease in Vesicles Derived from Bacteria of the Genus *Bacillus* by Metagenomic Analysis for Bacteria-Derived Vesicles in Blood of Liver Cancer Patient Blood samples obtained from 91 patients with liver cancer and 99 normal persons as normal controls matching the patients' sex and age were subjected to metagenomic analysis by extracting genes from vesicles present in the blood according to the method described in Example 2, followed by evaluating the distribution of vesicles derived from bacteria of the genus *Bacillus*. The evaluation result confirmed that, compared with the blood of a normal person, vesicles derived from bacteria of the genus *Bacillus* are significantly reduced in the blood of a gastric cancer] patient (normal person vs liver cancer patient: 0.37% vs 0.13%; fold change: 0.37; p=0.0002) (refer to FIG. 3).

Example 4. Confirmation of Decrease in Vesicles Derived from Bacteria of the Genus *Bacillus* by Metagenomic Analysis for Bacteria-Derived Vesicles in Blood of Bladder Cancer Patient Blood samples obtained from 96 patients with bladder cancer and 184 normal persons as normal controls matching the patients' sex and age were subjected to metagenomic analysis by extracting genes from vesicles present in the blood by the method described in Example 2, followed by evaluating the distribution of vesicles derived from bacteria of the genus *Bacillus*. The evaluation result confirmed that, compared with the blood of a normal person, the vesicles derived from bacteria of the genus *Bacillus* are significantly reduced in the blood of a bladder cancer patient (normal person vs bladder cancer patient: 0.38% vs 0.10%; fold change: 0.27; p=0.001) (refer to FIG. 4).

Example 5. Confirmation of Decrease in Vesicles Derived from Bacteria of the Genus *Bacillus* by Metagenomic Analysis for Bacteria-Derived Vesicles in Blood of Breast Cancer Patient Blood samples obtained from 96 patients with breast cancer and 192 normal persons as normal controls matching the patients' sex and age were subjected to metagenomic analysis by extracting genes from vesicles present in the blood according to the method described in Example 2, followed by evaluating the distribution of vesicles derived from bacteria of the genus *Bacillus*. The evaluation result confirmed that, compared with the blood of normal person, vesicles derived from bacteria of the genus *Bacillus* are significantly reduced in the blood of a breast cancer patient (normal person vs breast cancer: 0.59% vs 0.26%; fold change: 0.44; p=0.0006) (refer to FIG. 5).

Example 6. Confirmation of Decrease in Vesicles Derived from Bacteria of the Genus *Bacillus* by Metagenomic Analysis for Bacteria-Derived Vesicles in Blood of Ovarian Cancer Patient Blood samples obtained from 137 patients with ovarian cancer and 139 normal persons as normal controls matching the patients' sex and age were subjected to metagenomic analysis by extracting genes from vesicles present in the blood by the method described in Example 2, followed by evaluating the distribution of vesicles derived from bacteria of the genus *Bacillus*. The evaluation result confirmed that, compared with the blood of a normal person, the vesicles derived from bacteria of the genus *Bacillus* are significantly reduced in the blood of an ovarian cancer patient (normal person vs ovarian cancer patient: 0.61% vs 0.27%; fold change: 0.44; p=0.01) (refer to FIG. 6).

Example 7. Confirmation of Decrease in Vesicles Derived from Bacteria of the Genus *Bacillus* by Metagenomic Analysis for Bacteria-Derived Vesicles in Blood of Asthma Patient Blood samples obtained from 277 patients with asthma and 246 normal persons as normal controls matching the patients' sex and age were subjected to metagenomic analysis by extracting genes from vesicles present in the blood by the method described in Example 2, followed by evaluating the distribution of vesicles derived from bacteria of the genus *Bacillus*. The evaluation result confirmed that, compared with the blood of a normal person, the vesicles derived from bacteria of the genus *Bacillus* are significantly reduced in the blood of an asthma patient (normal person vs asthma patient: 0.47% vs 0.09%; fold change: 0.20; p<0.000001) (refer to FIG. 7).

Example 8. Confirmation of Decrease in Vesicles Derived from Bacteria of the Genus *Bacillus* by Metagenomic Analysis for Bacteria-Derived Vesicles in Blood of Atopic Dermatitis Patient Blood samples obtained from 25 patients with atopic dermatitis and 138 normal persons as normal controls matching the patients' sex and age were subjected to metagenomic analysis by extracting genes from vesicles present in the blood by the method described in Example 2, followed by evaluating the distribution of vesicles derived from bacteria of the genus *Bacillus*. The evaluation result confirmed that, compared with the blood of a normal person, the vesicles derived from bacteria of the genus *Bacillus* are significantly reduced in the blood of an atopic dermatitis patient (normal person vs atopic dermatitis patient: 0.10% vs 0.04%; fold change: 0.44; p=0.01) (refer to FIG. 8).

Example 9. Confirmation of Decrease in Vesicles Derived from Bacteria of the Genus *Bacillus* by Metagenomic Analysis for Bacteria-Derived Vesicles in Blood of Diabetic Patient Blood samples obtained from 73 patients with diabetes and 146 normal persons as normal controls matching the patients' sex and age were subjected to metagenomic analysis by extracting genes from vesicles present in the blood by the method described in Example 2, followed by evaluating the distribution of vesicles derived from bacteria of the genus *Bacillus*. The evaluation result confirmed that, compared with the blood of a normal person, the vesicles derived from bacteria of the genus *Bacillus* are significantly reduced in the blood of a diabetic patient (normal person vs diabetic patient: 0.46% vs 0.04%; fold change: 0.10; p<0.000001) (refer to FIG. 9).

Example 10. Confirmation of Decrease in Vesicles Derived from Bacteria of the Genus *Bacillus* by Metagenomic Analysis for Bacteria-Derived Vesicles in Blood of Cirrhosis Patient Blood samples obtained from 73 patients with cirrhosis and 146 normal persons as normal controls matching the patients' sex and age were subjected to metagenomic analysis by extracting genes from vesicles present in the blood by the method described in Example 2, followed by evaluating the distribution of vesicles derived from bacteria of the genus *Bacillus*. The evaluation result demonstrated that, compared with the blood of a normal person, the vesicles derived from bacteria of the genus *Bacillus* are significantly reduced in the blood of a cirrhosis patient (normal person vs cirrhosis patient: 0.54% vs 0.25%; fold change: 0.47; p=0.003) (refer to FIG. 10).

Example 11. Confirmation of Increase in Vesicles Derived from Bacteria of the Genus *Escherichia* by Metagenomic Analysis for Bacteria-Derived Vesicles in Blood of Diabetic Patient Blood samples obtained from 73 patients with diabetes and 146 normal persons as normal controls matching the patients' sex and age were subjected to metagenomic analysis by extracting genes from vesicles present in the blood by the method described in Example 2, followed by evaluating the distribution of vesicles derived from bacteria of the genus *Escherichia*. The evaluation result confirmed that, compared with the blood of a normal person, the vesicles derived from bacteria of the genus *Escherichia* are significantly increased in the blood of a diabetic patient (normal person vs diabetic patient: 0.008% vs 0.8.165%; fold change: 947.3; p<0.000001) (refer to FIG. 11).

Example 12. Isolation of Vesicles from *Bacillus subtilis* Culture Solution and Evaluation of Characteristics of the Vesicles To evaluate characteristics of the vesicles derived from bacteria of the genus *Bacillus*, characteristics of vesicles isolated from a culture solution of a *Bacillus subtilis* standard strain were evaluated. To isolate the vesicles, *Bacillus subtilis* was inoculated in 2 L of autoclaved brain-heart infusion broth (BD 237500) and incubated in a chamber such that an optical density (O.D.) reached 1.5 for 72 hours, and then the culture solution was subjected to ultracentrifugation (10,000×g) for 20 minutes to obtain a supernatant except a cell pellet. The supernatant was filtered sequentially using a 0.45 µm filter and a 0.22 µm filter, and approximately 14-fold concentrated using a Quixstand benchtop system. The culture solution was subjected to ultracentrifugation again at 150,000×g and 4° C. for 2 hours, thereby obtaining a pellet, and the pellet was dissolved in PBS to quantify a protein.

The morphology and size of the *Bacillus subtilis*-derived vesicles obtained from the *Bacillus subtilis* culture solution were observed and measured according to the above-described method. First, to evaluate the morphology of the vesicles, 50 µg/mL of a sample was obtained by protein quantification and subjected to observation under a JEM 1011 electron microscope (Jeol, Japan), confirming that, as shown in FIG. 12A, the *Bacillus subtilis*-derived vesicles are spherical. Subsequently, the 50 µg/mL of the sample was subjected to size measurement for the *Bacillus subtilis*-derived vesicles through dynamic light scattering (DLS) using Zetasizer Nano ZS (Malverk, UK). As a result, as shown in FIG. 12B, it can be seen that the average diameter of the *Bacillus subtilis*-derived vesicles ranged from 40 to 100 nm.

Example 13. Comparison of Difference in Inflammation Induction Between *Bacillus subtilis*-Derived Vesicles and *E. coli*-Derived Vesicles To evaluate the inflammation induction of the *Bacillus subtilis*-derived vesicles isolated by the method described in Example 12, using *E. coli*-derived vesicles, which is a pathogenic causative factor, as a positive control group, the inflammation induction in inflammatory cells, that is, a macrophage cell line (Raw 264.7) was compared. To this end, the macrophage cell line was treated with *E. coli*-derived vesicles (*E. coli* EV, 1 µg/mL), or various concentrations of *Bacillus subtilis* standard strain-derived vesicles (*Bacillus subtilis* EV, 0.1. 1 or 10 µg/mL) and *Bacillus subtilis* natto strain-derived vesicles (*Bacillus subtilis* natto EV, 0.1. 1 or 10 µg/mL), and after 12 hours, the concentrations of inflammatory cytokines such as IL-6 and TNF-α were measured through ELISA to compare an inflammation-inducing ability. Here, as a negative control (NC), PBS was treated.

As a result, as shown in FIG. 13, it was confirmed that, when *E. coli*-derived vesicles were treated, IL-6 secretion was induced, and when the *Bacillus subtilis* standard strain-derived vesicles or *Bacillus subtilis* natto strain-derived vesicles were treated, IL-6 secretion was not induced regardless of treatment concentration (refer to FIG. 13A). In addition, regarding TNF-α secretion, compared with *E. coli*-derived vesicles at the same concentration, it was confirmed that a TNF-α secretion ability caused by the *Bacillus subtilis* standard strain-derived vesicles or *Bacillus subtilis* natto-derived vesicles was considerably reduced (refer to FIG. 13B).

Example 14. Confirmation of Inflammatory Effect of *Bacillus subtilis*-Derived Vesicles on Inflammation Caused by *E. coli*-Derived Vesicles Among the bacteria of the genus *Escherichia*, representative bacteria *E. coli* is the main bacterium residing in surrounding environments as well as the large intestine, and has high antibiotic resistance. In addition, as the *E. coli*-derived vesicles were identified as the major causative factor of a chronic obstructive airway disease such as asthma or COPD, it was known as the major causative factor of a chronic inflammatory disease. Therefore, the anti-inflammatory effect of *Bacillus subtilis*-derived vesicles on the inflammation caused by *E. coli*-derived vesicles was evaluated. To this end, a macrophage cell line (Raw 264.7) was treated with *Bacillus subtilis* standard strain-derived vesicles (*B. subtilis* EV, 0.1, 1 or 10 µg/mL) or *Bacillus subtilis* natto strain-derived vesicles (*B. subtilis* natto EV, 0.1, 1 or 10 g/mL), and after 12 hours, macrophages were treated with *E. coli*-derived vesicles (1 µg/mL), followed by measurement of the concentrations of inflammatory cytokines such as IL-6 and TNF-α by ELISA. Here, as a negative control (NC), as described in Example 13, PBS was treated, as a positive control (PC), only *E. coli*-derived vesicles (1 µg/mL) were treated, and as a comparative group, *Lactobacillus plantarum*-derived vesicles (*Lactobacillus plantarum* EV, 1 µg/mL) known to have an anti-inflammatory effect were pre-treated under the same conditions as the *Bacillus subtilis*-derived vesicles.

Consequently, as shown in FIG. 14, IL-6 secretion caused by stimulation of *E. coli*-derived vesicles was inhibited to a similar level as *Lactobacillus plantarum*-derived vesicles due to the pre-treatment with *Bacillus subtilis* standard strain-derived vesicles, and more completely inhibited, compared to the *Lactobacillus plantarum*-derived vesicles, due to the pre-treatment with *Bacillus subtilis* standard strain- or *Bacillus subtilis* natto strain-derived vesicles (refer to FIG. 14A). In addition, it was observed that, in the case of *Lactobacillus plantarum*-derived vesicles, TNF-α secretion was not inhibited, whereas, in the cases of the *Bacillus* subtilis standard strain- and *Bacillus subtilis* natto strain-derived vesicles, TNF-α secretion was dose-dependently inhibited (refer to FIG. 14B). This result shows that inflammation generated by inflammatory mediators such as IL-6 and TNF-α was efficiently inhibited by the *Bacillus subtilis*-derived vesicles.

ing to the present invention can be effectively used for a method of diagnosing or predicting cancer, a chronic inflammatory disease or a metabolic disease, and a food, inhalant, cosmetic or pharmaceutical composition for preventing or treating cancer, a chronic inflammatory disease or a metabolic disease.

SEQUENCE LISTING

```
<160> NUMBER OF SEQ ID NOS: 2

<210> SEQ ID NO 1
<211> LENGTH: 50
<212> TYPE: DNA
<213> ORGANISM: Artificial Sequence
<220> FEATURE:
<223> OTHER INFORMATION: Forward primer for 16s rDNA
<220> FEATURE:
<221> NAME/KEY: MISC_FEATURE
<222> LOCATION: (42)
<223> OTHER INFORMATION: any nucleotide of DNA

<400> SEQUENCE: 1
tcgtcggcag cgtcagatgt gtataagaga cagcctacgg gnggcwgcag              50

<210> SEQ ID NO 2
<211> LENGTH: 55
<212> TYPE: DNA
<213> ORGANISM: Artificial Sequence
<220> FEATURE:
<223> OTHER INFORMATION: Reverse primer for 16s rDNA

<400> SEQUENCE: 2
gtctcgtggg ctcggagatg tgtataagag acaggactac hvgggtatct aatcc        55
```

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

INDUSTRIAL APPLICABILITY

The inventors confirmed that intestinal bacteria are not absorbed into a body, but bacteria-derived vesicles are absorbed into the body and systemically dispersed, and then excreted through the kidneys, the liver or the lungs, and also confirmed through metagenomic analysis for bacteria-derived vesicles present in the blood, urine or feces of a patient that vesicles derived from bacteria of the genus *Bacillus*, present in the blood of a patient with solid cancer such as liver cancer, bladder cancer, breast cancer or ovarian cancer, a chronic inflammatory disease such as asthma or atopic dermatitis, or a metabolic disease such as diabetes or liver cirrhosis are significantly less than those of a normal person.

In addition, when a *Bacillus subtilis* standard strain, which is one species of bacteria of the genus *Proteus*, and *Bacillus subtilis* natto, which is a *Bacillus subtilis* subtype, are cultured in vitro to isolate vesicles, and the vesicles are administered in vitro to inflammatory cells, it was observed that the secretion of inflammatory mediators due to pathogenic vesicles is significantly inhibited, showing that the vesicles derived from bacteria of the genus *Bacillus* accord-

The invention claimed is:

1. A method for inhibiting IL-6 or TNF-α secretion caused by inflammation factors in a subject in need thereof, comprising: administering a composition consisting of an effective amount of vesicles from *Bacillus subtilis* as an active ingredient and a pharmaceutically acceptable carrier, to a subject with inflammation caused by inflammation factors, wherein the vesicles themselves are an active ingredient to inhibit secretion of IL-6 or TNF-α, and wherein the vesicles are naturally occurring vesicles secreted by *Bacillus subtilis* and the vesicles have a cell wall.

2. The method of claim 1, wherein the composition is a pharmaceutical composition, a food composition or an inhalant composition.

3. The method of claim 1, wherein the inflammation is in asthma, chronic hepatitis or atopic dermatitis.

4. The method of claim 1, wherein the inflammation is mediated by IL-6 or TNF-α.

5. The method of claim 4, wherein the TNF-α-mediated inflammatory disease is hair loss, rheumatoid arthritis, or inflammatory enteritis.

6. The method of claim 1, wherein the vesicles are isolated from a culture solution of the *Bacillus subtilis*.

7. The method of claim 1, wherein the vesicles are isolated from food produced through culture by addition of the *Bacillus subtilis*.

* * * * *